(12) United States Patent
VanZandt et al.

(10) Patent No.: US 6,225,314 B1
(45) Date of Patent: May 1, 2001

(54) INHIBITION OF MATRIX METALLOPROTEASES BY SUBSTITUTED BIARYL OXOBUTYRIC ACIDS

(75) Inventors: Michael C. VanZandt, Guilford; David R. Brittelli, Branford; Brian R. Dixon, Woodbridge, all of CT (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/343,142

(22) Filed: Jun. 29, 1999

Related U.S. Application Data

(62) Division of application No. 08/856,693, filed on May 15, 1997, now Pat. No. 5,925,637.

(51) Int. Cl.$^7$ .................. A61K 31/495; C07D 237/32
(52) U.S. Cl. ............................. 514/248; 544/235
(58) Field of Search ............... 544/235; 514/248

(56) References Cited

U.S. PATENT DOCUMENTS

| 5,861,427 | 1/1999 | Kluender et al. | 514/417 |
| 5,874,473 | 2/1999 | Kluender et al. | 514/570 |
| 5,925,637 | * 7/1999 | VanZandt et al. | 514/243 |

FOREIGN PATENT DOCUMENTS 9519961   7/1995  (WO)  ............ C07C/323/41

OTHER PUBLICATIONS

Sahoo, et al., Inhibition of Matrix Metalloproteinases by N–Carboxyalkyl Dipeptides: Enhanced Potency and Selectivity with Substituted P$_1$' Homophenylanines, Biorganic & Medicinal Chemistry Letters, 5(20), 2441–2446 (1995).
Child, et al., Fenbufen, a New Anti–Inflammatory Analgesic: Synthesis and Structure–Activity Relationships of Analogs, Journal of Pharmaceutical Sciences, 66(4), 466–476 (1977).

* cited by examiner

Primary Examiner—Floyd D. Higel
Assistant Examiner—Ebenezer Sackey

(57) ABSTRACT

Matrix metalloprotease inhibiting compounds, pharmaceutical compositions thereof and a method of disease treatment using such compounds are presented. The compounds of the invention have the generalized formulas:

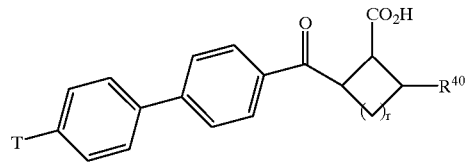

wherein r is 0–2, T is selected from

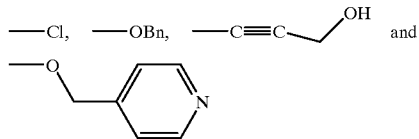

and $R^{40}$ is a mono- or bi-heterocyclic structure.

These compounds are useful for inhibiting matrix metalloproteases and, therefore, combating conditions to which MMP's contribute, such as osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempero mandibular joint disease, demyelating diseases of the nervous system, tumor metastasis or degenerative cartilage loss following traumatic joint injury, and coronary thrombosis from arteriosclerotic plaque rupture. The present invention also provides pharmaceutical compositions and methods for treating such conditions.

7 Claims, No Drawings

INHIBITION OF MATRIX METALLOPROTEASES BY SUBSTITUTED BIARYL OXOBUTYRIC ACIDS

This application is a division of Ser. No. 08/856,693 filed May 15, 1997 now U.S. Pat. No. 5,925,637.

BACKGROUND OF THE INVENTION

1. Field of the Invention

This invention relates to enzyme inhibitors, and more particularly, to novel substituted biaryl oxobutyric acid compounds or derivatives thereof useful for inhibiting matrix metalloproteases.

2. Description of the Related Art

The matrix metalloproteases (a.k.a. matrix metalloendoproteinases or MMPs) are a family of zinc endoproteinases which include, but are not limited to, interstitial collagenase (a.k.a. MMP-1), stromelysin (a.k.a. proteoglycanase, transin, or MMP-3), gelatinase A (a.k.a. 72 kDa-gelatinase or MMP-2) and gelatinase B (a.k.a. 95 kDa-gelatinase or MMP-9). These MMPs are secreted by a variety of cells including fibroblasts and chondrocytes, along with natural proteinaceous inhibitors known as TRMPs tissue Inhibitor of MetalloProteinase).

All of these MMPs are capable of destroying a variety of connective tissue components of articular cartilage or basement membranes. Each MMP is secreted as an inactive proenzyme which must be cleaved in a subsequent step before it is able to exert its own proteolytic activity. In addition to the matrix destroying effect, certain of these MMPs such as MMP-3 have been implemented as the in vivo activator for other MMPs such as MMP-1 and MMP-9 (Ito, et al., Arch Biochem Biophys. 267, 211 (1988); Ogata, et al., J. Biol. Chem. 267, 3581 (1992)). Thus, a cascade of proteolytic activity can be initiated by an excess of MMP-3. It follows that specific MMP-3 inhibitors should limit the activity of other MMPs that are not directly inhibited by such inhibitors.

It has also been reported that MMP-3 can cleave and thereby inactivate the endogenous inhibitors of other proteinases such as elastase (Winyard, et al., FEBS Letts. 279 1, 91 (1991)). Inhibitors of MMP-3 could thus influence the activity of other destructive proteinases by modifying the level of their endogenous inhibitors.

A number of diseases are thought to be mediated by excess or undesired matrix-destroying metalloprotease activity or by an imbalance in the ratio of the MMPs to the TIMPs. These include: a) osteoarthritis (Woessner, et al., J. Biol. Chem., 259(6), 3633 (1984); Phadke, et al., 3. Rheumatol. 10, 852 1983)), b) rheumatoid arthritis (Mullins, et al., Biochim. Biophys. Acta 695, 117 (1983)); Woolley, et al., Arthritis Rheum. 20, 1231 (1977); Gravallese, et al., Arthritis Rheum. 34, 1076 (1991)), c) septic arthritis (Williams, et al., Arthritis Rheum. 33, 533 (1990)), d) tumor metastasis (Reich, et al., Cancer Res., 48, 3307 (1988), and Matisian, et al., Proc. Nat'l. Acad. Sci., USA 83, 9413, (1986)), e) periodontal diseases (Overall, et al., J. Periodontal Res. 22, 81 (1987)), f) corneal ulceration (Burns, et al., Invest. Opthalmol. Vis. Sci. 30, 1569 (1989)), g) proteinuria (Baricos, et al., Biochem. J. 254, 609 (1988)), h) coronary thrombosis from atherosclerotic plaque rupture (Henney, et al., Proc. Nat'l. Acad. Sci., USA 88, 8154 (1991)), 1) aneurysmal aortic disease (Vine, et al., Clin. Sci. 81, 233 (1991)), j) birth control (Woessner, et al., Steroids 54, 491 (1989)), k) dystrophobic epidermolysis bullosa (Kronberger, et al., J. Invest Dermatol. 79, 208 (1982)), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688 (1988)).

The need for new therapies is especially important in the case of arthritic diseases. The primary disabling effect of osteoarthritis (OA), rheumatoid arthritis (RA) and septic arthritis is the progressive loss of articular cartilage and thereby normal joint function. No marketed pharmaceutical agent is able to prevent or slow this cartilage loss, although nonsteroidal anti-inflammatory drugs (NSAIDs) have been given to control pain and swelling. The end result of these diseases is total loss of joint function which is only treatable by joint replacement surgery. MMP inhibitors are expected to halt or reverse the progression of cartilage loss and obviate or delay surgical intervention.

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Mullins, et al., Biochim. Biophys. Acta 695, 177 (1983); Ray, et al., Eur. Respir. J. 7, 2062 (1994); Birkedal-Hansen, et al., Crit. Rev. Oral Biol. Med. 4, 197 (1993).

Furthermore, it was demonstrated that inhibition of degradation of extracellular matrix by the native matrix metalloprotease inhibitor TIMP-2 (a protein) arrests cancer growth (DeClermk, et al., Cancer Res. 52, 701 (1992)) and that TIMP-2 inhibits tumor-induced angiogenesis in experimental systems (Moses, et al. Science 248, 1408 (1990)). For a review, see DeClerck, et al., Ann. N. Y. Acad. Sci. 732, 222 (1994). It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726 (1994)) and prolongs the survival of mice bearing human ovarian carcinoma xenografts (Davies, et. al., Cancer Res. 53, 2087 (1993)). The use of this and related compounds has been described in Brown, et al., WO-9321942 A2 (931111).

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 Al; Beckett, et al., WO-9519956 Al; Beckett, et al., WO-9519957 Al; Beckett, etal., WO-9519961 Al; Brown, et al., WO-9321942 A2; Crimmin, et al., WO-9421625 Al;

Dickens, et al., U.S. Pat. No. 4,599,361; Hughes, et al., U.S. Pat. No. 5,190,937; Broadhurst, et al., EP 574758 A1; Broadhurst, et al,. EP 276436; and Myers, et al., EP 520573 A1. The preferred compounds of these patents have peptide backbones with a zinc complexing group (hydroxamic acid, thiol, carboxylic acid or phosphinic acid) at one end and a variety of sidechains, both those found in the natural amino acids as well as those with more novel functional groups. Such small peptides are often poorly absorbed, exhibiting low oral bioavailability. They are also subject to rapid proteolytic metabolism, thus having short half lives. As an example, batimartat, the compound described in Brown, et al., WO-9321942 A2, can only be given intra peritoneally.

Certain 3-biphenoylpropanoic and 4-biaryloylbutanoic acids are described in the literature as anti-inflammatory, anti-platelet aggregation, anti-phlogistic, anti-proliferative, hypolipidemic, antirheumatic, analgesic, and hypocholester-olemic agents. In none of these examples is a reference made to MMP inhibition as a mechanism for the claimed therapeutic effect. Certain related compounds are also used as intermediates in the preparation of liquid crystals.

Specifically, Tomcufcik, et al., U.S. Pat. No. 3,784,701 claims certain substituted benzoylpropionic acids to treat inflammation and pain. These compounds include 3-biphenoylpropanoic acid (a.k.a fenbufen) shown below.

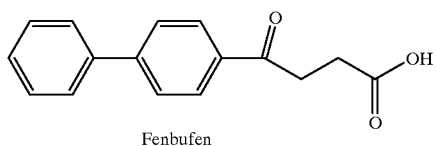

Fenbufen

Child, et al., J. Pharm. Sci., 66, 466 (1977) describes structure-activity relationships of several analogs of fenbufen. These include several compounds in which the biphenyl ring system is substituted or the propanoic acid portion is substituted with phenyl, halogen, hydroxyl or methyl, or the carboxylic acid or carbonyl functions are converted to a variety of derivatives. No compounds are described which contain a 4'-substituted biphenyl and a substituted propanoic acid portion combined in one molecule. The phenyl (compounds XLIX and LXXVII) and methyl (compound XLVII) substituted compounds shown below were described as inactive.

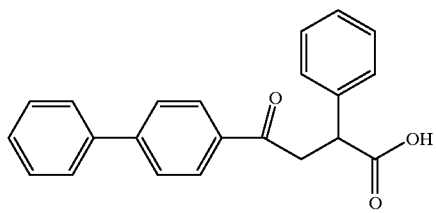

XLIX

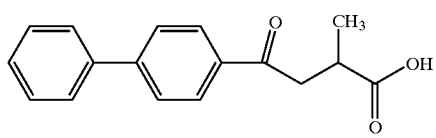

XLVII

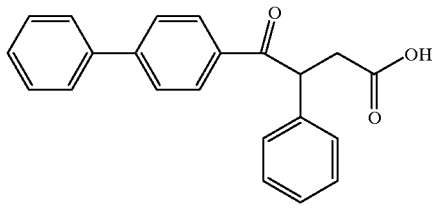

LXXVII

Kameo, et al., Chem. Pharm. Bull., 36, 2050 (1988) and Tomizawa, et al., JP patent 62132825 A2 describe certain substituted 3-biphenoylpropionic acid derivatives and analogs thereof including the following. Various compounds with other substituents on the propionic acid portion are described, but they do not contain biphenyl residues.

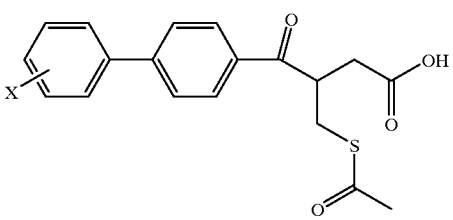

wherein X=H, 4'-Br, 4'-Cl, 4'-$CH_3$, or 2'-Br.

Cousse, et al., Eur. J. Med. Chem., 22, 45 (1987) describe the following methyl and methylene substituted 3biphenoyl-propanoic and -propenoic acids. The corresponding compounds in which the carbonyl is replaced with either $CH_2OH$ or $CH_2$ are also described.

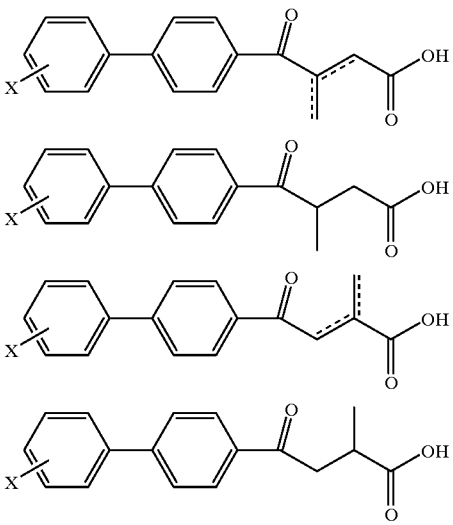

wherein X=H, Cl, Br, $CH_3O$, F, or $NH_2$.

Nichl, et al. DE patent 1957750 also describes certain of the above methylene substituted biphenoylpropanoic acids.

El-Hashash, et al., Revue Roum. Chim. 23, 1581 (1978) describe products derived from β-aroyl-acrylic acid epoxides including the following biphenyl compound. No compounds substituted on the biphenyl portion are described.

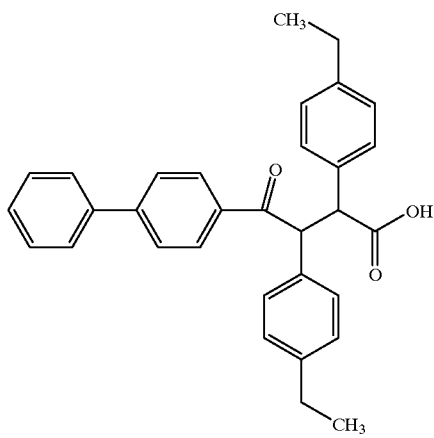

Kitamura, et al., JP patent 60209539 describes certain biphenyl compounds used as intermediates for the production of liquid crystals including the following. The biphenyl is not substituted in these intermediates.

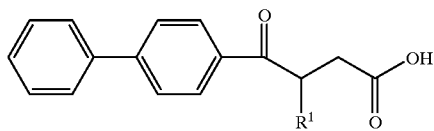

wherein $R^1$ is an alkyl of 1–10 carbons.

Thyes, et al., DE patent 2854475 uses the following compound as an intermediate. The biphenyl group is not substituted.

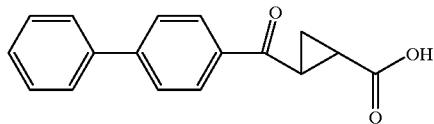

Sammour, et al., Egypt J. Chem. 15, 311 (1972) and Couquelet, et al., Bull. Soc. Chim. Fr. 9, 3196 (1971) describe certain dialkylamino substituted biphenoylpropanoic acids including the following. In no case is the biphenyl group substituted.

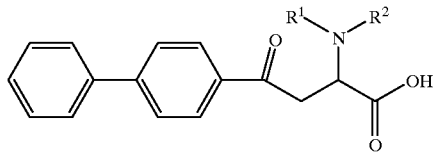

wherein $R^1$, $R^2$=alkyl, benzyl, H, or, together with the nitrogen, morpholinyl.

Others have disclosed a series of biphenyl-containing carboxylic acids, illustrated by the compound shown below, which inhibit neural endopeptidase (NEP 24.11), a membrane-bound zinc metalloprotease (Stanton, et al., Bioorg. Med. Chem. Lett. 4, 539 (1994); Lombaert, et al., Bioorg. Med. Chem. Lett. 4, 2715 (1994); Lombaert, et al., Bioorg. Med. Chem. Lett. 5, 145 (1995); Lombaert, et al., Bioorg. Med. Chem. Lett. 5, 151 (1995)).

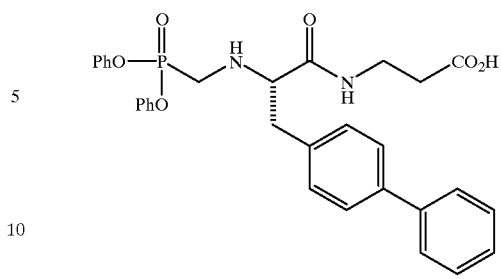

It has been reported that N-carboxyalkyl derivatives containing a biphenylethylglycine, illustrated by the compound shown below, are inhibitors of stromelysin-1 (MMP-3), 72 kDA gelatinase (MMP-2) and collagenase (Durette, et al., WO-9529689).

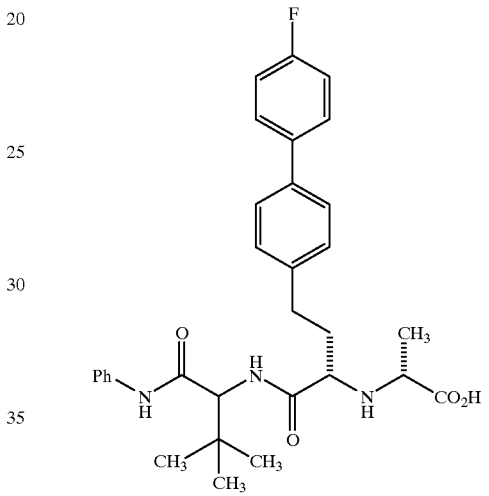

It would be desirable to have effective MMP inhibitors which possess improved bioavailability and biological stability relative to the peptide-based compounds of the prior art, and which can be optimized for use against particular target MMPs. Such compounds are the subject of the present application.

The development of efficacious MMP inhibitors would afford new therapies for diseases mediated by the presence of, or an excess of MMP activity, including osteoarthritis, rheumatoid arthritis, septic aithritis, tumor metastasis, periodontal diseases, corneal ulcerations, and proteinuria. Several inhibitors of MMPs have been described in the literature, including thiols (Beszant, et al., J. Med. Chem. 36, 4030 (1993), hydroxamic acids (Wahl, et al. Bioorg. Med. Chem. Lett. 5, 349 (1995) Conway, et al. J. Exp. Med. 182, 449 (1995); Porter, et al., Bioorg. Med. Chem. Lett. 4, 2741 (1994); Tomczuk, et al., Bioorg. Med. Chem. Lett. 5, 343 (1995); Castelhano, et al., Bioorg. Med. Chem. Lett. 5, 1415 (1995)), phosphorous-based acids (Bird, et al. J. Med. Chem. 37, 158 (1994); Morphy, et al., Bioorg. Med. Chem. Lett. 4, 2747 (1994); Kortylewicz, et al., J. Med. Chem. 33, 263 (1990)), and carboxylic acids (Chapman, et al. J. Med. Chem. 36, 4293 (1993); Brown, et al. J. Med. Chem. 37, 674 (1994); Morphy, et al., Bioorg. Med. Chem. Lett. 4, 2747 (1994); Stack, et al., Arch. Biochem. Biophys. 287, 240 (1991); Ye, et al., J. Med. Chem. 37, 206 (1994); Grobelny, et al., Biochemistry 24, 6145 (1985); Mookhtiar, et al., Biochemistry 27, 4299 (1988)). However, these inhibitors generally contain peptidic backbones, and thus usually exhibit low oral bioactivity due to poor absorption and short half lives due to rapid proteolysis. Therefore, there remains a need for improved MMP inhibitors.

SUMMARY OF THE INVENTION

This invention provides compounds having matrix metalloprotease inhibitory activity. These compounds are useful for inhibiting matrix metalloproteases and, therefore, combating conditions to which MMP's contribute. Accordingly, the present invention also provides pharmaceutical compositions and methods for treating such conditions.

The compounds described relate to a method of beating a mammal comprising administering to the mammal a matrix metalloprotease inhibiting amount of a compound according to the invention sufficient to:

(a) alleviate the effects of osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempero mandibular joint disease, demyelating diseases of the nervous system;

(b) retard tumor metastasis or degenerative cartilage loss following traumatic joint injury, (c) reduce coronary thrombosis from athrosclerotic plaque rupture; or (d) temporarily reduce fertility (i.e., act as effective birth control agents).

The compounds of the present invention are also useful scientific research tools for studying functions and mechanisms of action of matrix metalloproteases in both in vivo and in vitro systems. Because of their MMP-inhibiting activity, the present compounds can be used to modulate MMP action, thereby allowing the researcher to observe the effects of reduced MMP activity in the experimental biological system under study.

This invention relates to compounds having matrix metalloprotease inhibitory activity and the generalized formula:

(T)$_x$A—B—D—E—G  (L)

In the above generalized formula (L), (T)$_x$A represents a substituted or unsubstituted aromatic 6-membered ring or heteroaromatic 5–6 membered ring containing 1–2 atoms of N, O, or S. T represents one or more substituent groups, the subscript x represents the number of such substituent groups, and A represents the aromatic or heteroaromatic ring.

In the generalized formula (L), B represents an aromatic 6-membered ring or a heteroaromatic 5–6 membered ring containing 1–2 atoms independently selected from the group of N, O, or S. It is referred to as the B ring or B unit. When N is employed in conjunction with either S or O in the B ring, these heteroatoms are separated by at least one carbon atom.

In the generalized formula (L), D represents

In the generalized formula (L), E represents a chain of n carbon atoms bearing m substituents R$^6$ in which the R$^6$ groups are independent substituents, or constitute spiro or nonspiro rings. Rings may be formed in two ways: a) two groups R$^6$ are joined, and taken together with the chain atom(s) to which the two R$^6$ group(s) are attached, and any intervening chain atoms, constitute a 3–7 membered ring, or b) one group R$^6$ is joined to the chain on which this one group R$^6$ resides, and taken together with the chain atom(s) to which the R$^6$ group is attached, and any intervening chain atoms, constitutes a 3–7 membered ring. The number n of carbon atoms in the chain is 2 or 3, and the number m of R$^6$ substituents is an integer of 1–3. The number of carbons in the totality of R$^6$ groups is at least two.

Each group R$^6$ is alkyl, alkenyl, alkynyl, heteroaryl, non-aromatic cyclic, and combinations thereof optionally substituted with one or more heteroatoms. In the In the generalized formula (L), E preferably represents a linear or cyclic alkyl moiety substituted with a mono- or bi-heterocyclic ring structure.

In the generalized formula (L), G represents —PO$_3$H$_2$, —M

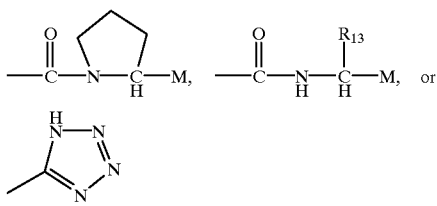

in which M represents —CO$_2$H, —CON(R$^{11}$)$_2$, wherein R$^{11}$ is H or sample alkyl, or —CO$_2$R$^{12}$, wherein R$^{12}$ is lower alkyl and R$^{13}$ represents any of the side chains of the 19 noncyclic naturally occurring amino acids.

Pharmaceutically acceptable salts of these compounds are also within the scope of the invention.

In most related reference compounds of the prior art the biphenyl portion of the molecule is unsubstituted, and the propanoic or butanoic acid portion is either unsubstituted or has a single methyl or phenyl group. Presence of the larger phenyl group has been reported to cause prior art compounds to be inactive as anti-inflammatory analgesic agents. See, for example, Child, et al., J. Pharm. Sci. 66, 466(1977). By contrast, it has now been found that compounds which exhibit potent MMP inhibitory activity contain a substituent of significant size on the propanoic or butanoic portion of the molecule. The biphenyl portions of the best MMP inhibitors also preferably contain a substituent on the 4'-position, although when the propanoic or butanoic portions are optimally substituted, the unsubstituted biphenyl compounds of the invention have sufficient activity to be considered realistic drug candidates.

The foregoing merely summarizes certain aspects of the present invention and is not intended, nor should it be construed, to limit the invention in any way. All of the patents and other publications recited in this specification are hereby incorporated by reference in their entirety.

DESCRIPTION OF THE PREFERRED EMBODIMENTS

More particularly, the compounds of the present invention are materials having matrix metalloprotease inhibitory activity and the generalized formula:

(T)$_x$A—B—D—E—G  (L)

in which (T)$_x$A represents a substituted or unsubstituted aromatic or heteroaromatic moiety selected from the group consisting of:

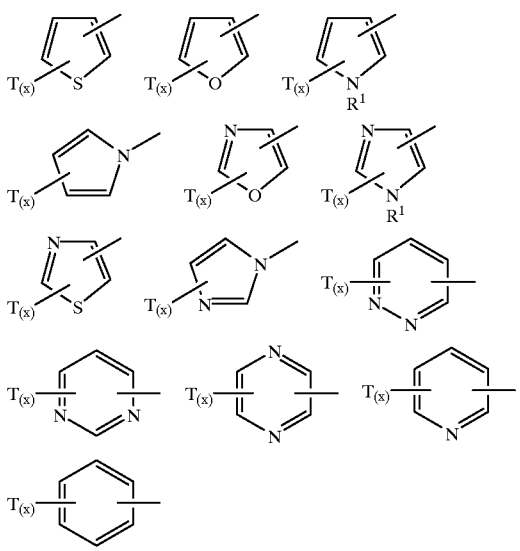

in which R¹ represents H or alkyl of alkyl of 1–3 carbons.

Throughout this application, in the displayed chemical structures, an open bond indicates the point at which the structure joins to another group. For example,

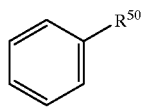

where $R^{50}$ is

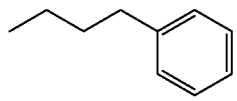

is the structure

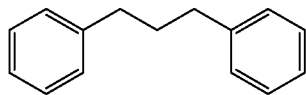

In the above structures, for $(T)_xA$ the aromatic ring is referred to as the A ring or A unit, and T represents a substituent group, referred to as a T group or T unit. Preferably 1.

The substituent group T can also be an acetylene containing moiety with the general formula:

where n is 1–4 and $R^{30}$ is selected from the group consisting of: HO—, MeO—, N(n-Pr)$_2$—, CH$_3$CO$_2$—, CH$_3$CH$_2$OCO$_2$—, HO$_2$C—, OHC—, Ph—, 3—HO—Ph—, and PhCH$_2$O—, provided that when $R^{30}$ is Ph or 3—HO—Ph, n=0.

The B ring of generalized formula (L) is a substituted or unsubstituted aromatic or heteroaromatic ring, in which any substituents are groups which do not cause the molecule to fail to fit the active site of the target enzyme, or disrupt the relative conformations of the A and B rings, such that they would be detrimental. Such substitutents may be moieties such as lower alkyl, lower alkoxy, CN, NO$_2$, halogen, etc. but are not to be limited to such groups.

In the generalized formula (L), B represents an aromatic or heteroaromatic ring selected from the group consisting of:

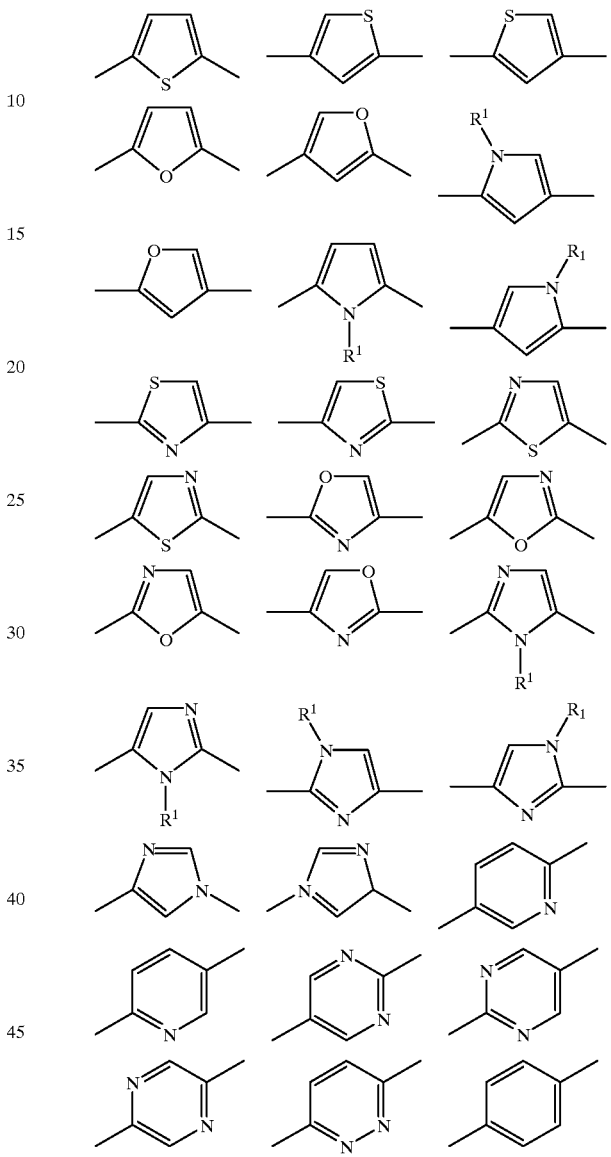

in which R¹ is defined as above. These rings are referred to as the B ring or B unit.

In an alternative embodiment, compounds of the general formula (L) include those in which the combination $(T)_x$—A—B has the structure:
where Z may be $(CH_2)_e$—$C_6H_4$—$(CH_2)_f$ or $(CH_2)_g$, e=0–8, f=0–5 and g=0–14, r is 0–6. $R^{15}$ may be a straight, or cyclic alkyl group of 6–12 carbons atoms, preferably of 7–11 carbon atoms, and optionally may bear one or more pharmaceutically acceptable substituents which are discussed more fully below.

$R^{15}$ may also be a polyether of the formula $R^{32}H$ $(C_2H_4O)_h$ in which the subscript "h" is 1 or 2, and the group $R^{32}$ is a straight, branched or cyclic alkyl group of 1–5 carbon atoms, preferably of 1–3 carbon atoms and straight, or phenyl, or benyl. $R^{32}$ optionally may bear one or more pharmaceutically-acceptable substituents.

$R^{15}$ may also be a substituted alkynyl group of the formula:

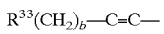

in which the subscript "b" is 1–10 and the group $R^{33}$ is H—, HO— or $R^{34}$O— and the group is preferably the HO— group. $R^{34}$ may be an alkyl group of 1–3 carbon atoms, or phenyl or benzyl. $R^{33}$ optionally may bear one or more pharmaceutically-acceptable substituents.

$R^{15}$ may also be H, Cl, MeO or wherein n is 0–4, $R^{17}$ is $C_2H_5$, allyl, or benzyl.

In the generalized formula (L), D represents the moieties:

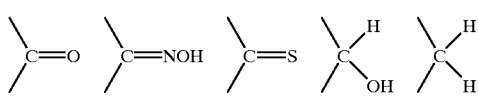

In the generalized formula (L), the moiety between D and G shown by the following formula:

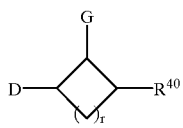

wherein r is 0–2 and $R^{40}$ is a mono- or bi- heterocyclic structure. When r=0 the above structure takes the form

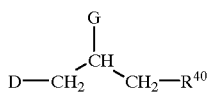

When r is 1 or 2, a cyclobutyl or cyclopentyl ring is formed, respectively. Each ring of the mono- or bi- heterocyclic structures comprise 5–7 membered rings substituted with 1–3 heteroatoms independently selected from N, S, and O; one or two carbons of the ring are optionally carbonyl carbons; any sulfur of the ring is optionally —S(O)— or —S(O)$_2$—; one or more ring members are optionally substituted with one or two methyl groups, In addition, aryl or heteroaryl portions of any of the T or $R^6$ groups optionally may bear up to two such as —(CH$_2$)$_y$C(R$^{11}$)(R$^{12}$)OH, —(CH$_2$)$_y$OR$^{11}$, —(CH$_2$)$_y$SR$^{11}$, —(CH$_2$)$_y$S(O)R$^{11}$, —(CH$_2$)$_y$S(O)$_2$R$^{11}$, —(CH$_2$)$_y$SO$_2$N(R$^{11}$)$_2$, —(CH$_2$)$_y$N(R$^{11}$)$_2$, —(CH$_2$)$_y$N(R$^{11}$)COR$^{12}$, —OC(R$^{11}$)$_2$O— in which both oxygen atoms are connected to the aryl ring.

The B ring is preferably a 1,4-phenylene or 2,5-thiophene ring, most preferably 1,4-phenylene.

The D unit is most preferably a carbonyl group.

In the E unit, r is preferably 0 or 2 and $R^{40}$ is preferably one of the following:

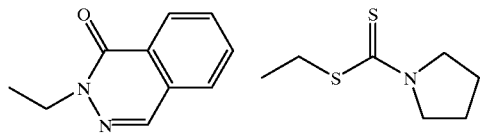

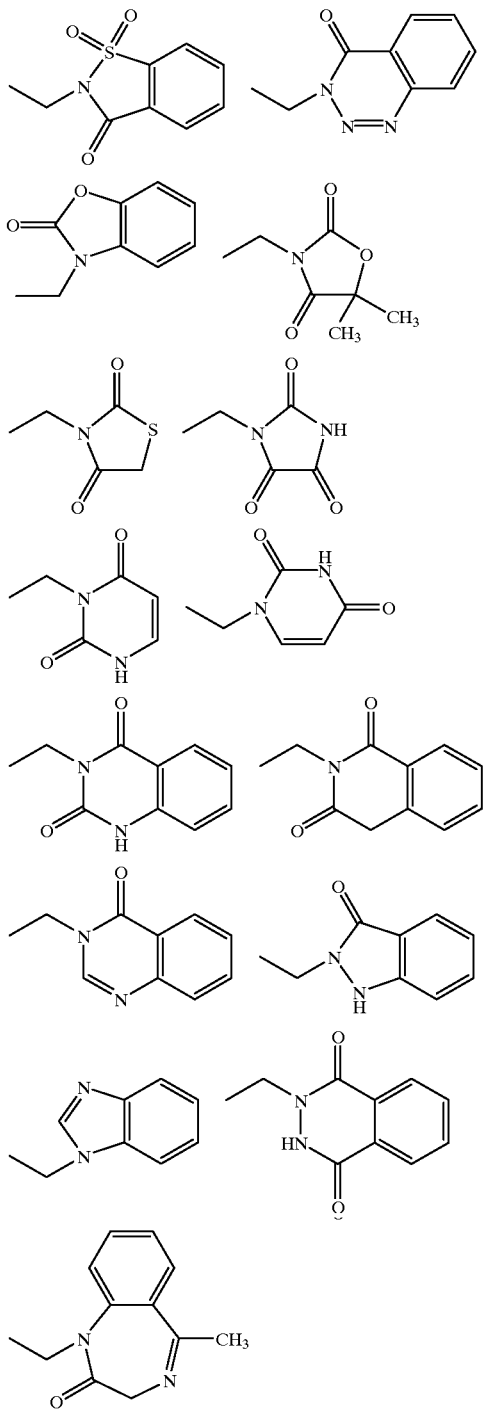

or PhCH$_2$OCH$_2$OCH$_2$—.

The G unit is most preferably a carboxylic acid group and is attached to the E unit at the 2 position, i.e., the carbon atom of the E unit beta to the D unit.

It is to be understood that as used herein, the term "alkyl" means straight, branched, cyclic, and polycyclic materials. The term "haloalkyl" means partially or fully halogenated alkyl groups such as —(CH$_2$)$_2$Cl, —CF$_3$ and —C$_6$F$_{13}$ for example.

In the generalized formula (L), the A and B rings are preferably phenyl and phenylene, respectively, the A ring preferably bears at least one substituent group T preferably located on the position furthest from the position of the A ring which is connected to the B ring, the D unit is preferably a carbonyl group, and the G unit is preferably a carboxyl group.

Certain alternative embodiments include compounds having matrix metalloproteinase inhibitory activity and the following generalized formula:

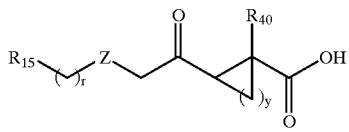

where $Z=(CH_2)_e$—$C_6H_4$—$(CH_2)_g$ or $(CH_2)_g$, $e=0-8$, $f=0-5$, $g=0-14$, r is 0–6 and where y is 0, 2, or 3.

$R^{15}$ may be H, Cl, MeO or wherein n is 0–4, $R^{17}$ is $C_2H_5$, allyl or benzyl, and $R^{40}$ is one of:

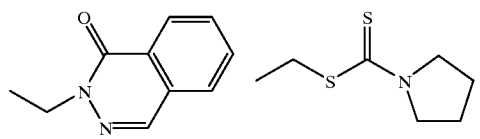

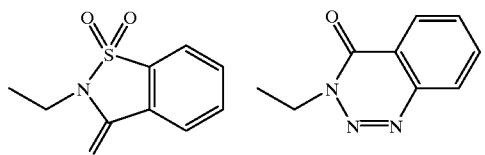

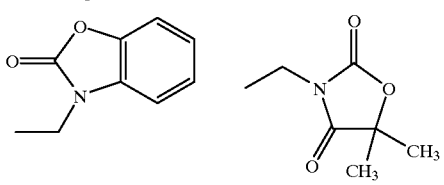

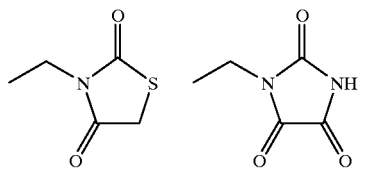

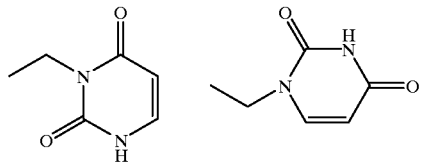

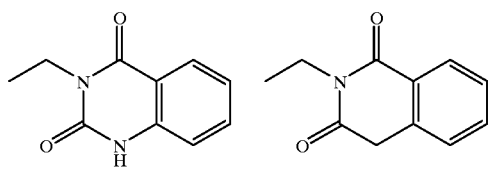

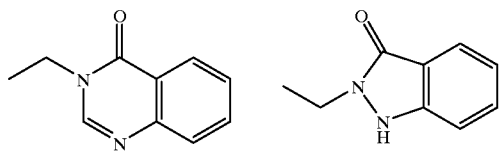

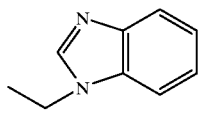

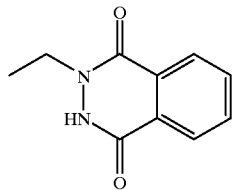

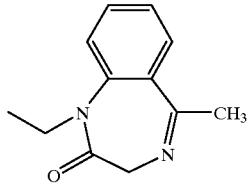

and —$CH_2OCH_2OCH_2Ph$.

The most preferred compounds of generalized formula (L) are

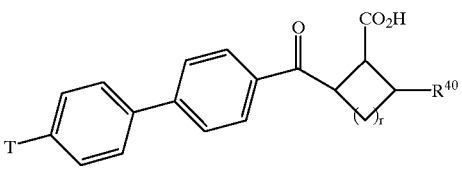

wherein T is selected from a group consisting of:

—Cl,   —OBn,   —C≡C—OH   and

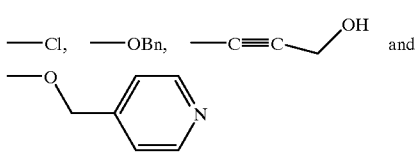

r is 0–2, and $R^{40}$ is selected from the group consisting of:

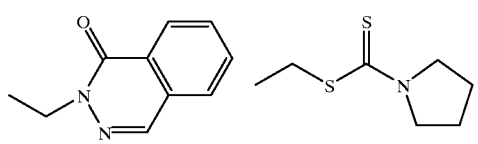

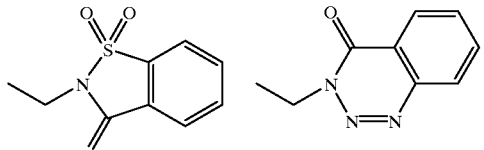

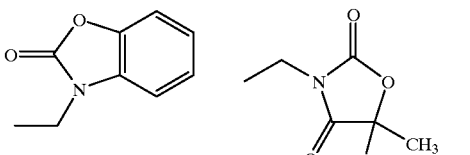

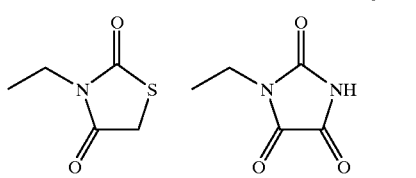

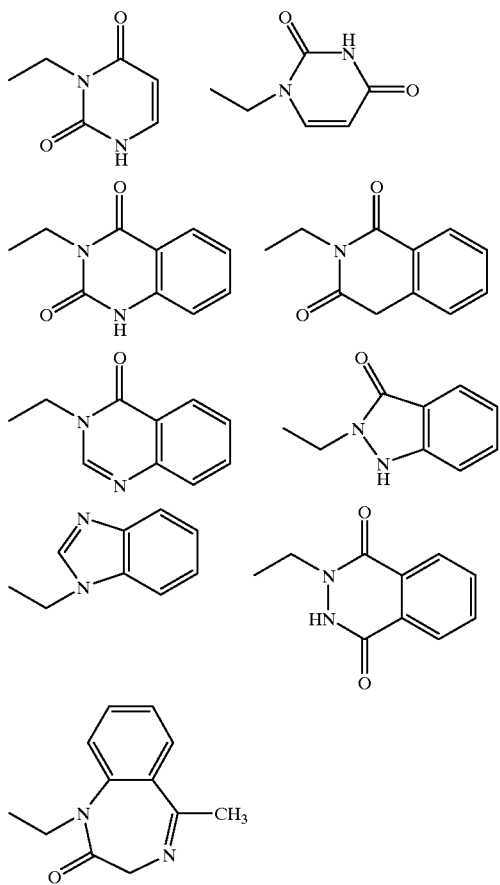

and —CH$_2$OCH$_2$OCH$_2$Ph.

The invention also relates to certain intermediates useful in the synthesis of some of the claimed inhibitors. These intermediates are compounds having the generalized formula

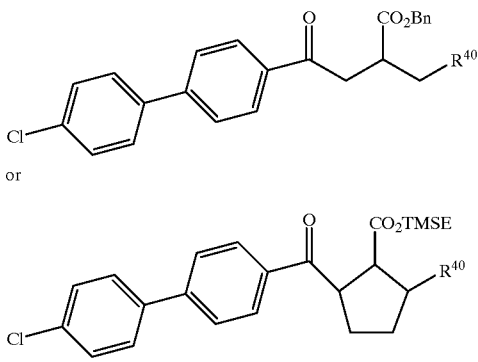

where Bn is benzyl, TMSE is trimethylsilyl ethyl and R$^{40}$ is as defined above.

Those skilled in the art will appreciate that many of the compounds of the invention exist in enantiomeric or diastereomeric forms, and that it is understood by the art that such stereoisomers generally exhibit different activities in biological systems. This invention encompasses all possible stereoisomers which possess inhibitory activity against an MMP, regardless of their stereoisomeric designations, as well as mixtures of stereoisomers in which at least one member possesses inhibitory activity.

The most prefered compounds of the present invention are as indicated and named in the list below:

I) 2-[(4'-chloro[1,1'-biphenyl]-4-yl)carbonyl]-5-[(4-oxo-1,2,3-benzotriazin-3(4H)-yl)methyl]-cyclopentanecarboxylic acid, II) 2-[(4'-chloro[1,1'-biphenyl)-4-yl)carbonyl]-5-[phenoxymethoxymethyl]-cyclopentanecarboxylic acid, III) 2-[4'-chloro[1,1'-biphenyl]-4-yl)carbonyl]-5-[[(1-pyrrolidinylthioxomethyl)thio]methyl]-cyclopentanecarboxylic acid, IV) 2-[(4'-chloro[1,1'-biphenyl]-4-yl)carbonyl]-5-[(1,1-dioxido-3-oxo-1,2-benzisothiazol-2(3H)-yl)methyl]-cyclopentanecarboxylic acid, V) 2-[(4'-chloro[1,1'-biphenyl]-4-yl)carbonyl]-5-[1-oxo-2 (1H)-phthalazinyl)methyl]-cyclopentanecarboxylic acid, VI) 2-[4'-chloro [1,1'-biphenyl]-4-yl)carbonyl]-5-[(2-oxo-3 (2H)-benzoxazolyl)methyl]-cyclopentanecarboxylic acid, VII) 2-[(4'-chloro[1,1'-biphenyl]-4-yl)carbonyl]-5-[5,5-dimethyl-2,4-dioxo-3-oxazolidinylmethyl]-cyclopentanecarboxylic acid, VIII) 2-[(4'-chloro[1,1'-biphenyl]-4-yl)carbonyl]-5-[(2,4-dioxo-3-thiazolidinyl)methyl]-cyclopentanecarboxylic acid, IX) 2-[(4'-chloro[1,1'-biphenyl]-4-yl)carbonyl]-5-[2,4,5-trioxo-1-imidazolidinyl)methyl]-cyclopentanecarboxyl acid X) 2-[(4'-chloro(1,1'-biphenyl]-4-yl)carbonyl]-5-[(3,6-dihydro-2,6-dioxo-1(2H)-pyrimidinyl)methyl]-cyclopentanecarboxylic acid, XI) 2-[(4'-chloro[1,1'-biphenyl]-4-yl)carbonyl]-5-[3,4-dihydro-2,4-dioxo-1(2H)-pyrimidinyl)methyl]-cyclopentanecarboxylic acid, XII) 2-[(4'-chloro[1,1'-biphenyl]-4-yl)carbonyl]-5-[(1,4-dihydro-2,4-dioxo-3(2H)-quinazolinyl)methyl]-cyclopentanecarboxylic acid, XIII) 2-[(4'-chloro[1,1'-biphenyl]-4-yl)carbonyl]-5-[3,4-dihydro-1,3-dioxo-2(1H)-isoquinolinyl)methyl]-cyclopentanecarboxylic acid, XIV) 2-[(4'-chloro[1,1'-biphenyl]-4-yl)carbonyl]-5-[(1,4-dihydro-4-oxo-3(2H)-quinazolinyl)methyl]-cyclopentanecarboxylic acid, XV) 2-[4'-chloro[1,1'-biphenyl]-4-yl)carbonyl]-5-[(1,3-dihydro-3-oxo-2H-indazol-2-yl)methyl]-cyclopentanecarboxylic acid, XVI) 2-[(4'-chloro[1,1'-biphenyl]-4-yl)carbonyl]-5-[2,3-dihydro-1H-benzimidazol-1-yl)methyl]-cyclopentanecarboxylic acid, XVII) 2-[(4'-chloro[1,1'-biphenyl]-4-yl)carbonyl]-5-[(3,4-dihydro-1,4-dioxo-2(1H)-phthalazinyl)methyl]-cyclopentanecarboxylic acid, XVIII) R/S α-[2-(4'-chloro[1,1'-biphenyl]-4yl)2-oxoethyl]-1-oxo-2(1H)-phthalazinebutanoic acid, XIX) R-α-[2-(4'-chloro[1,1'-biphenyl]-4-yl)-2-oxoethyl]-1-oxo-2(1H)-phthalazinebutanoic acid, XX) S-α-[2-(4'-chloro[1,1 '-biphenyl]-4-yl)-2-oxoethyl]-1-oxo-2(1H)-phthalazinebutanoic acid, XXI) α-[2-(4'-chloro[1,1'-biphenyl]-4-yl)-2-oxoethyl]-4-oxo-1,2,3,-Benzotriazine-3(4H)-butanoic acid, and XXII) α-[2-(4'-chloro[1,1'-biphenyl]-4-yl)-2-oxoethyl]-2,3-dihydro-5-methyl-2-oxo-1H-1,4-benzodiazepine-1-butanoic acid.

General Preparative Methods

The compounds of the invention may be prepared readily by use of known chemical AdO reactions and procedures. Nevertheless, the following general preparative methods are presented to aid the reader in synthesizing the inhibitors, with more detailed particular examples being presented below in the experimental section describing the working examples. AU variable groups of these methods are as described in the generic description if they are not specifically defined below. The variable subscript n is independently defined for each method. When a variable group with a given symbol (i.e $R^9$) is used more than once in a given structure, it is to be understood that each of these groups may be independently varied within the range of definitions for that symbol.

General Method A—The compounds of this invention in which the rings A and B are substituted phenyl and phenylene respectively are conveniently prepared by use of a Friedel-Crafts reaction of a substituted biphenyl MII with an activated acyl-containing intermediate such as the succinic or glutaric anhydride derivative MIII or acid chloride MIV in the presence of a Lewis acid catalyst such as aluminum trichloride in an aprotic solvent such as 1,1,2,2-tetrachloroethane. The well known Friedel-Crafts reaction can be accomplished with use of many alternative solvents and acid catalysts as described by Berliner, Org. React, 5, 229, 1949 and Heaney, Comp. Org. Synth. 2, 733, 1991.

If the anhydride MIII is monosubstituted or multiply-substituted in an unsymmetrical way, the raw product MI-A often exists as a mixture of isomers via attack of the anhydride from either of the two carbonyls. The resultant isomers can be separated into pure forms by crystallization or chromatography using standard methods known to those skilled in the art.

When they are not commercially available, the succinic anhydrides MIII can be prepared via a Stobbe Condensation of a dialkyl succinate with an aldehyde or ketone (resulting in side chain $R^6$), followed by catalytic hydrogenation, hydrolysis of a hemiester intermediate to a diacid, and then conversion to the anhydride MIII by reaction with acetyl chloride or acetic anhydride. Alternatively, the hemiester intermediate is converted by treatment with thionyl chloride or oxalyl chloride to the acid chloride MIV. For a review of the Stobbe condensation, including lists of suitable solvents and bases see Johnson and Daub, Org. React., 6, 1, 1951.

This method, as applied to the preparation of MIII ($R^6$=H, isobutyl and H, n-pentyl), has been described Wolanin, et al., U.S. Pat. No. 4,771,038.

MI-A-3. The trans compounds Ml-A4 are then prepared by treatment of MI-A-3 with a base such as DBU in THF. The substituted four member ring starting material anhydrides such as MIII-A-1 are formed in a photochemical 2+2 reaction as shown below. This method is especially useful for the preparation of compounds in which $R^{14}$ is acetoxy or acetoxymethylene. After the subsequent Friedel-Crafts reaction the acetate can be removed by basic hydrolysis and the carboxyl protected by conversion to 2-(trimethylsilylethyl) ester. The resultant intermediate with $R^{14}$=$CH_2OH$ can be converted to invention compounds with other $R^{14}$ groups by using procedures described in General Method G.

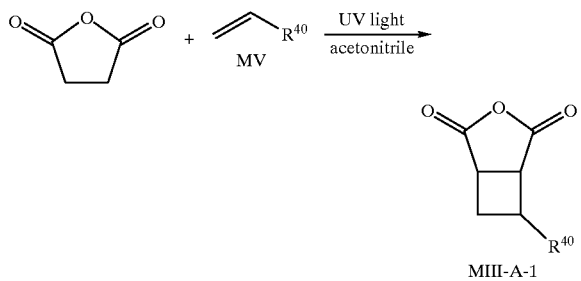

The Friedel-Crafis method is also usefu when double bonds are found either between C-2 and C-3 of a succinoyl chain (from maleic anhydride or 1-cyclopentene-1,2-dicarboxylic anhydride, for example) or when a double bond is found in a side chain, such as in the use of itaconic anhydride as starting material to yield products in which two $R^6$ groups are found on one chain carbon together to form an exo-methylene (=$CH_2$) group. Subsequent uses of these compounds are described in Methods D.

General Method B—Alternatively the compounds MI can be prepared via a reaction sequence involving mono-alkylation of a dialkyl malonate MVI with an alkyl halide to form intermediate MVII, followed by alkylation with a halomethyl biphenyl ketone MVIII to yield intermediate MIX. Compounds of structure MIX are then hydrolyzed with aqueous base and heated to decarboxylate the malonic acid intermediate and yield MI-B-2 (Method B-1). By using

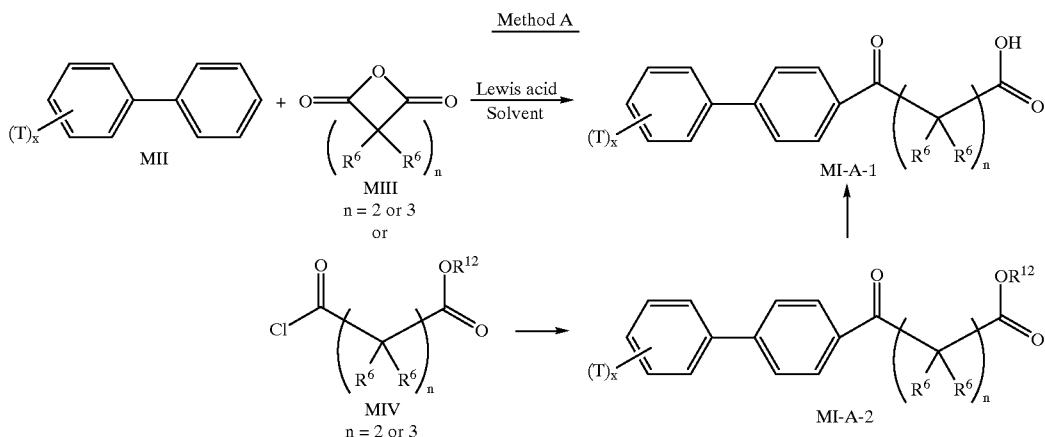

Method A is especially useful for the preparation of cyclic compounds such as MI-A-3, in which two $R^6$ groups are connected in a methylene chain to form a 3–7 member ring. Small ring (3–5 member) anhydrides are readily available only as cis isomers which yield cis invention compounds one equivalent of aqueous base the esters MN-B-2 with $R^{12}$ as alkyl are obtained, and using more than two equivalents of base the acid compounds ($R^{12}$=H) are obtained. Optionally, heat is not used and the diacid or acid-ester MI-B-1 is obtained.

Alternatively, the diester intermediate MIX can be heated with a strong acids such as concentrated hydrochloric acid in acetic acid in a sealed tube at about 110° C. for about 24 hr to yield MI-B-1 ($R^{12}$=H). Alternatively, the reaction of MVI with MVIII can be conducted before that with the alkyl halide to yield the same MIX (Method B-2).

Alternatively, a diester intermediate MIX which contains $R^{12}$=allyl, can be exposed to Pd catalysts in the presence of isomers when Method A yields mixtures. Method B is especially useful when the side chains $R^6$ contain aromatic or heteroaromatic rings that may participate in intramolecular acylation reactions to give side products if Method A were to be used. This method is also very useful when the $R^6$ group adjacent to the carboxyl of the final compound contains heteroatoms such as oxygen, sulfur, or nitrogen, or more complex functions such as imide rings.

METHOD B

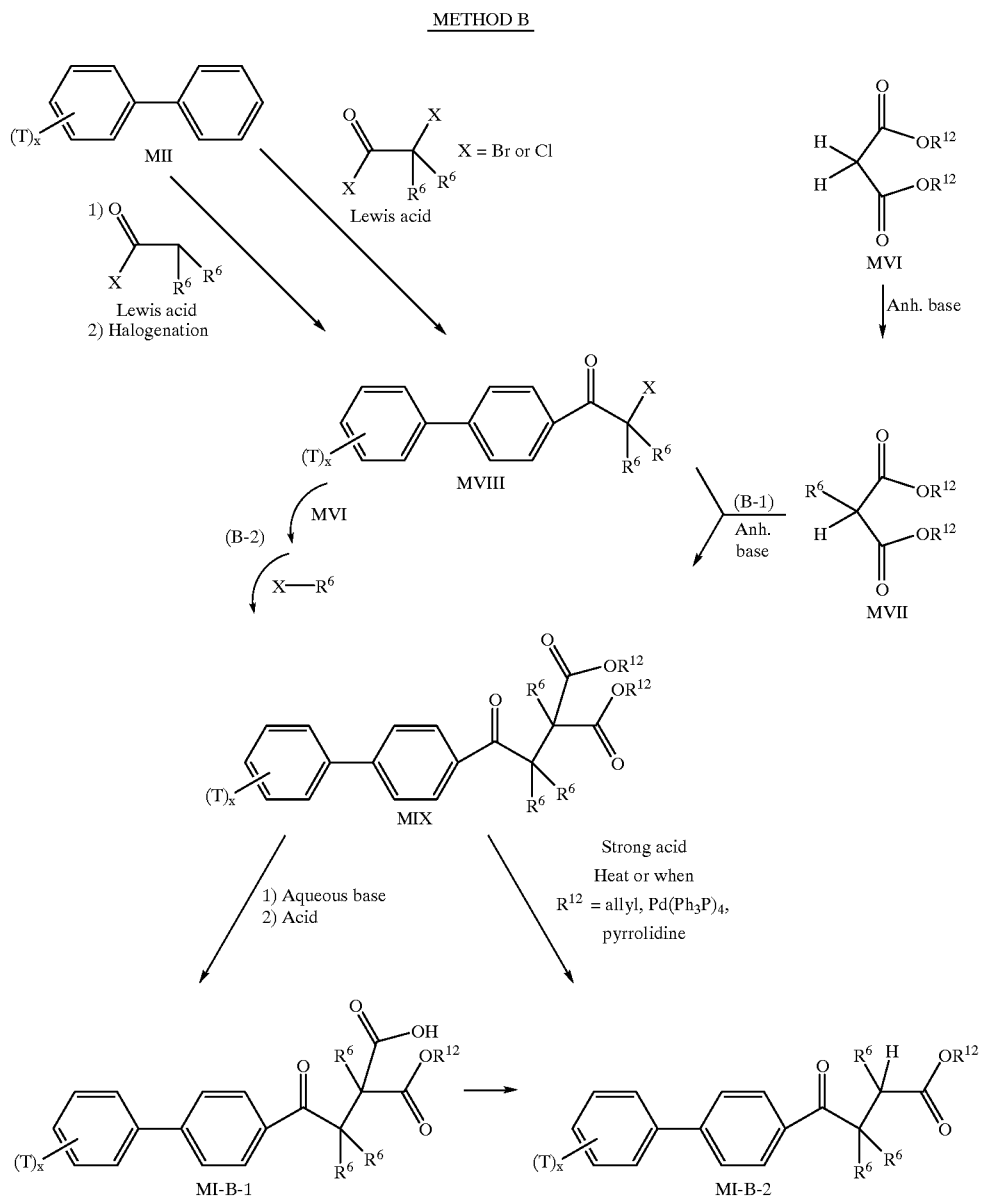

pyrrolidine to yield MI-B-2 ($R^{12}$=H) (Dezeil, Tetrahedron Lett. 28, 4371, 1990).

Intermediates MVII are formed from biphenyls MII in a Friedel-Craft reaction with haloacetyl halides such as bromoacetyl bromide or chloroacetyl chloride. Alternatively, the biphenyl can be reacted with acetyl chloride or acetic anhydride and the resultant product halogenated with, for example, bromine to yield intermediates MVI (X=Br).

Method B has the advantage of yielding single regio

When $R^6$ contains selected functional groups Z, malonate MVII can be prepared by alkylating a commercially available unsubstituted malonate with prenyl or allyl halide, subject this product to ozonalysis with reductive work-up, and the desired z group can be coupled via a Mitsunobu reaction (Mitsunobu, Synthesis 1, 1981). Alternatively, the intermediate alcohol can be subjected to alkylation conditions to provide malonate MVII containing the desired Z group.

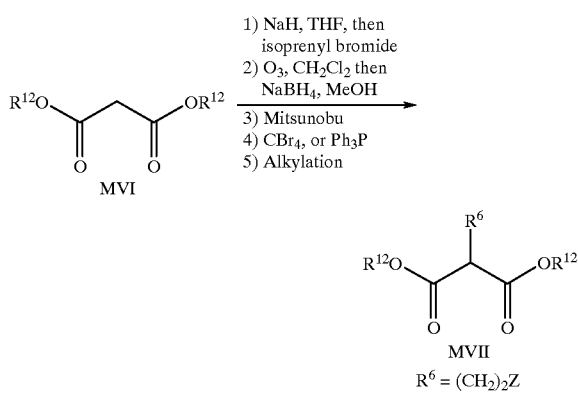

General Method C—Especially useful is the use of chiral HPLC to separate the enantiomers of racemic product mixtures (see, for example, Arit, et al., Chem. Int Ed. Engl. 12, 30 (1991)). The compounds of this invention can be prepared as pure enantiomers by use of a chiral auxiliary route. See, for example, Evans, Aldrichimica Acta, 15(2), 23, 1982 and other similar references known to one skilled in the art.

General Method D—Compounds in which $R^6$ are alkyl- or aryl- or heteroaryl- or acyl- or a heteroarylcarbonyl-thiomethylene are prepared by methods analogous to those described in the patent WO 90/05719. Thus substituted itaconic anhydride MXVI (n=1) is reacted under Friedel-Crafts conditions to yield acid MI-D-1 which can be separated by chromatography or crystallization from small amounts of isomeric MI-D-5. Alternatively, MI-D-5s are obtained by reaction of invention compounds MI-D-4 (from any of Methods A through C) with formaldehyde in the presence of base.

Compounds MI-D-1 or MI-D-5 are then reacted with a mercapto derivative MXVII or MXVIII in the presence of catalyst such as potassium carbonate, ethyldiisobutylamine, tetrabutylammonium fluoride or free radical initiators such as azobisisobutyronitile (AIBN) in a solvent such as diethylformamide or tetrahydrofuran to yield invention compounds MI-D-2, MI-D-3, MI-D-6, or MI-D-7.

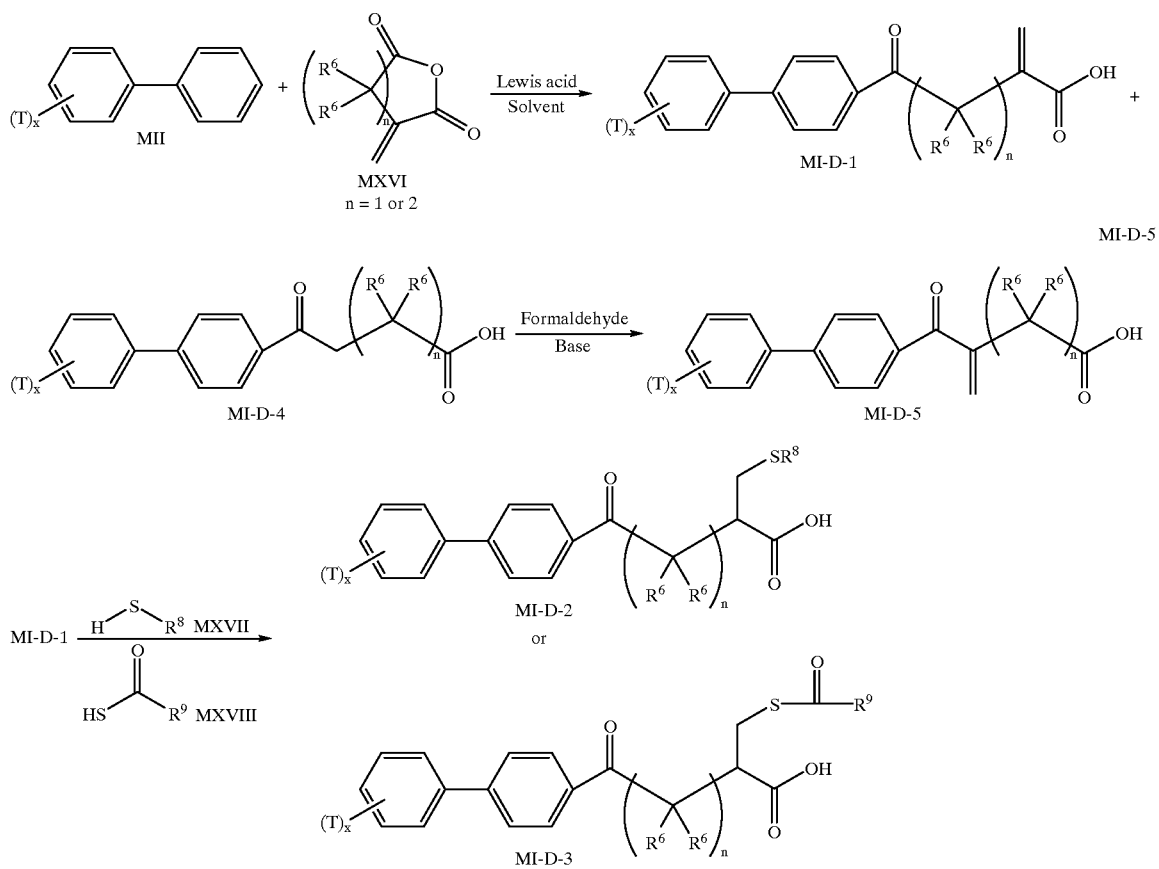

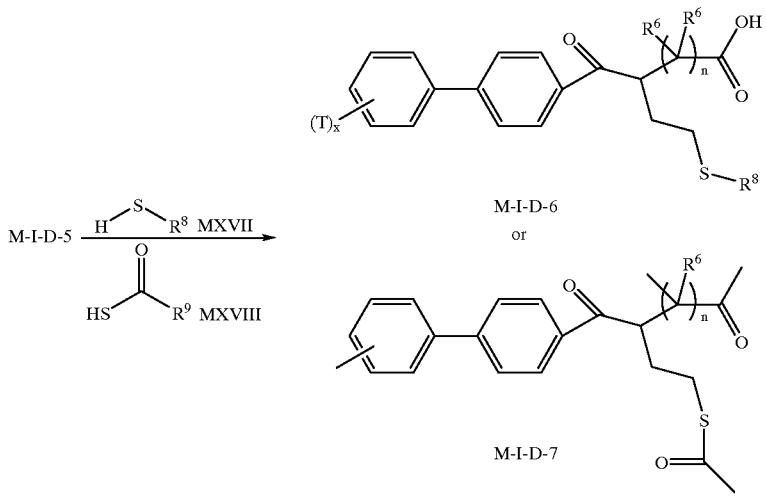

General Method E—Biaryl compounds such as those of this application may also be prepared by Suzuki or Stille cross-coupling reactions of aryl or heteroaryl metallic compounds in which the metal is zinc, tin, magnesium, lithium, boron, silicon, copper, cadmium or the like with an aryl or heteroaryl halide or triflate (trifluoromethane-sulfonate) or the like. In the equation below either Met or X is the metal and the other is the halide or triflate (OTf). Pd(com) is a soluble complex of palladium such as tetrakis(triphenylphosphine)palladium(O) or bis-(triphenylphosphine)palladium(E) chloride. These methods are well known to those skilled in the art. See, for example, Suzuki, Pure Appl. Chem. 63, 213 (1994); Suzuki, Pure Appl. Chem. 63, 419 (1991); and Farina and Roth, "Metal-Organic Chemistry" Volume 5 (Chapter 1), 1994.

The starting materials MXXIII (B=1,4-phenylene) are readily formed using methods analogous to those of methods A, B, C, or D but using a halobenzene rather Man a biphenyl as staring material. When desired, the materials in which X is halo can be converted to those in which X is metal by reactions well known to those skilled in the art, such as treatment of a bromo intermediate with hexamethylditin and palladium tetrakistriphenylphosphine in toluene at reflux to yield the trimethyltin intermediate. The starting materials MXXIII (B=heteroaryl) are most conveniently prepared by method C but using readily available heteroaryl rather than biphenyl starting materials. The intermediates MXXII are either commercial or easily prepared from commercial materials by methods well known to those skilled in the art.

Method E

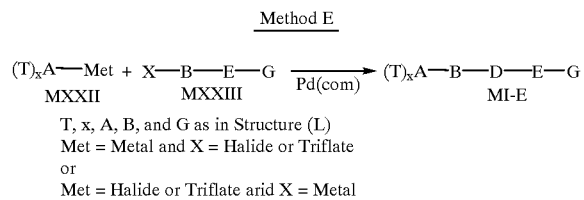

T, x, A, B, and G as in Structure (L)
Met = Metal and X = Halide or Triflate
or
Met = Halide or Triflate arid X = Metal These general methods are useful for the preparation of compounds for which Friedel-Crafts reactions such as those of Methods A, B, C, or D would lead to mixtures with various biaryl acylation patterns. Method E is also especially useful for the preparation of products in which the aryl groups, A or B, contain one or more heteroatoms (heteroaryls) such as those compounds that contain thiophene, furan, pyridine, pyrrole, oxazole, thiazole, pyrimidine or pyrazine rings or the like instead of phenyls.

General Method F—When the $R^6$ groups of method F form together a 4–7 member carbocyclic ring as in Intermediate MXXV below, the double bond can be moved out of conjugation with the ketone group by treatment with two equivalents of a strong base such as lithium diisopropylamide or lithium hexamethylsilylamide or the like followed by acid quench to yield compounds with the structure MXVI. Reaction of MXXVI with mercapto derivatives using methods analogous to those of General Method D then leads to cyclic compounds MI-F-I or MI-F-2.

Method F

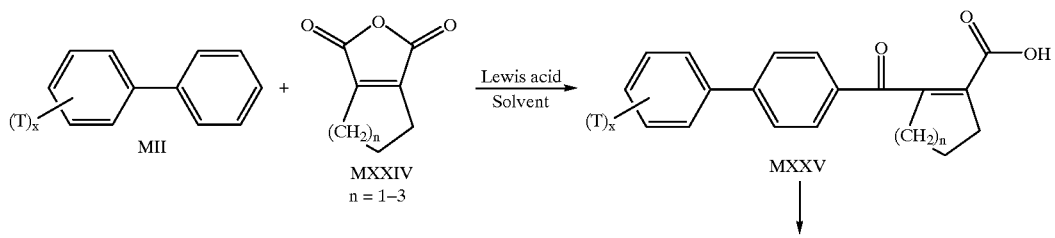

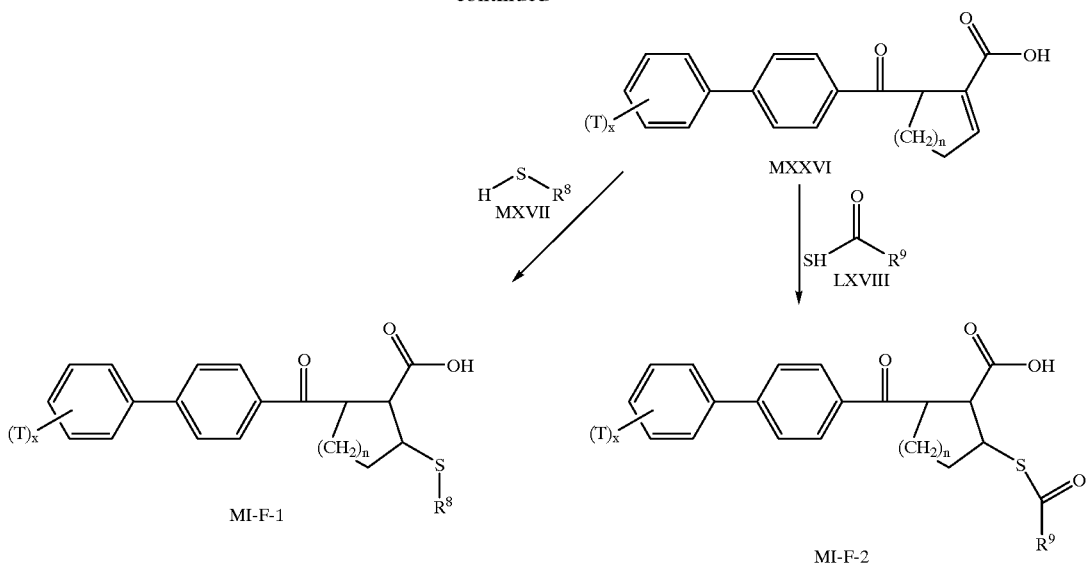

General Method G—The compounds of this invention in which two $R^6$ groups are joined to form a substituted 5-member ring are most conveniently prepared by method G. In this method acid CLII (R=H) is prepared using the protocols described in Tetrahedron 37, Suppl., 411 (1981). The acid is protected as an ester [eg. R=benzyl (Bn) or 2-(trimethylsilyl)ethyl (TMSE)] by use of coupling agents such as 1-(3-dimethylaminopropyl)-3-ethylcarbodiimide hydrochloride and procedures well known to those skilled in the art. Substituted bromobiphenyl CIII is converted to its Grignard reagent by treatment with magnesium and reacted with CLII to yield alcohol CVI. Alcohol CVI is eliminated via base treatment of its mesylate by using conditions well known to those skilled in the art to yield olefin CVII. Alternatively CIII is converted to a trimethyltin intermediate via initial metallation of the bromide with n-butyllithium at low temperature (−78° C.) followed by treatment with chlorotrimethyltin and CI is converted to an enoltriflate (CII) by reaction with 2-[N,N-bis(trifluoromethylsulfonyl) amino]-5-chloropyridine in the presence of a strong aprotic base. The tin and enoltriflate intermediates are then coupled in the presence of a $Pd^0$ catalyst, CuI and $AsPh_3$ to yield directly intermediate CVII. Ozonolysis of CVII (workup with methylsufide) yields aldehyde CVIII. Alternatively treatment with $OsO_4$ followed by $HIO_4$ converts CVII to CVIII.

Method G

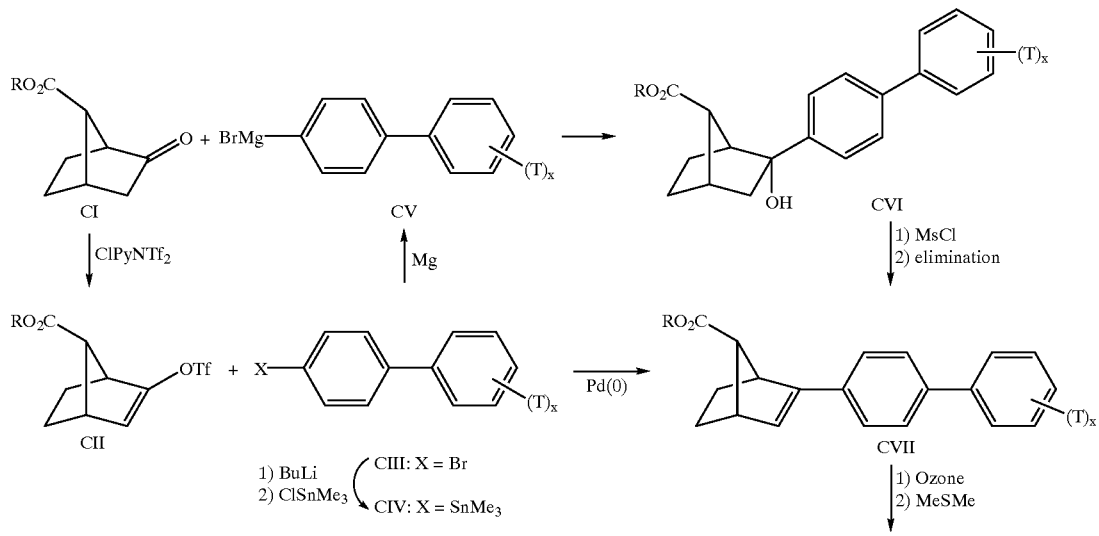

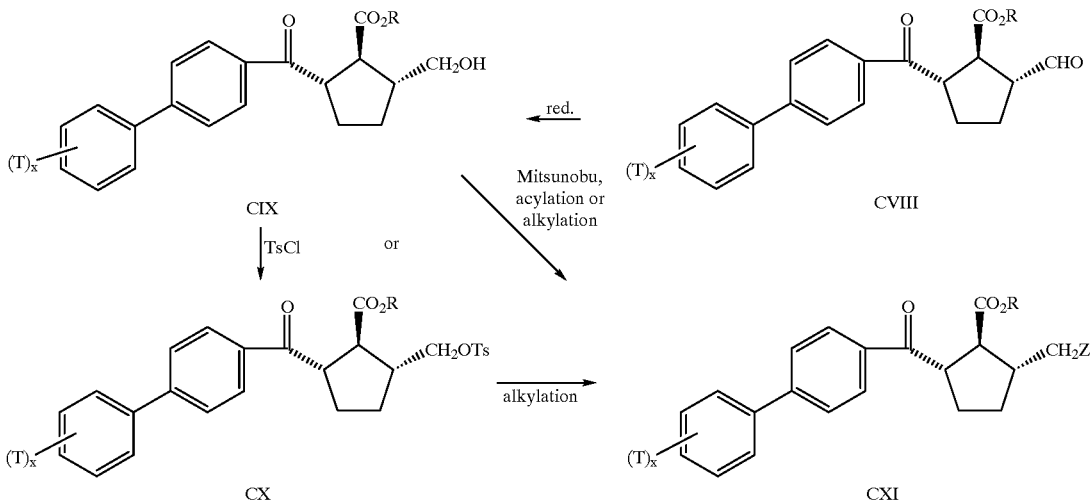

Conversion of key intermediate CVIII to the targeted patent compounds is accomplished in several ways depending on the identity of side chain function Z. Reaction of CVIII with Wittig reagents followed by hydrogenation yields products in which Z is alkyl and or arylalkyl. Selective reduction of aldehyde CVIII with a reducing agent such as lithium tris [(3-ethyl-3pentyl)oxy]aluminum hydride (LTEPA) yields alcohol CIX. The alcohol is converted to phenyl ethers or a variety of heteroatom substituted derivatives used to generate sidechain Z via the Mitsunobu reaction using conditions well known to those skilled in the art (see Mitsunobu, Synthesis, 1 (1981)). Alternatively the alcohol of CIX is converted to a leaving group such as tosylate (CX) or bromide by conditions well known to those skilled in the art and then the leaving La group is displaced by an appropriate nucleophile. Several examples of this type of reaction can be found in Norman, et al., J. Med. Chem. 37, 2552 (1994). Direct acylation of the alcohol CIX yields invention compounds in which Z=OAcyl and reaction of the alcohol with various allcyl halides in the presence of base yields alkyl ethers. In each case a final step is removal of acid blocking group R to yield acids (R=H) by using conditions which depend on the stability of R and Z, but in all cases well known to those skilled in the art such as removal of benzyl by base hydrolysis or of 2-(trimethylsilyl)ethyl by treatment with tetrabutylammonium fluoride.

General Method H—Amides of the acids of the invention compounds can be prepared from the acids by treatment in an appropriate solvent such as dichloromethane or dimethylformamide with a primary or secondary amine and a coupling agent such as dicyclohexylcarbodiimide. These reactions are well known to those skilled in the art. The amine component can be simple alkyl or arylalkyl substituted or can be amino acid derivatives in which the carboxyl is blocked and the amino group is free.

General Method I—The compounds of this invention in which $(T)_x$ is an alkynyl or substituted alkynyl are prepared according to general method I (Austin, J. Org. Chem. 46, 2280 (1981)). Intermediate MX is prepared according to methods A, B, C, D or G by starting with commercial MII (T=Br). Reaction of MX with substituted acetylene MXI in the presence of Cu(I)/palladate reagent gives invention compound MI-I-1. In certain cases, $R^3$ may be an alcohol blocked as trialkylsilyl. In such cases the silyl group can be removed by treatment with acids such as trifluoroacetic acid or HF - pyridine reagent.

Method I

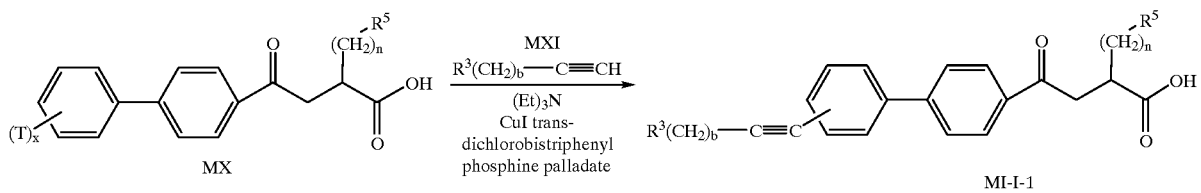

Suitable pharmaceutically acceptable salts of the compounds of the present invention include addition salts formed with organic or inorganic bases. The salt forming ion derived from such bases can be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamnine and N,N-dibenzylethylenediamine, lower alkylamines such as methylamine, t-butylarine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

These and other salts which are not necessarily physiologically acceptable are useful in isolating or purifying a product acceptable for the purposes described below. For example, the use of commercially available enantiomerically pure amines such as (+)-cinchonine in suitable solvents can yield salt crystals of a single enatiomer of the invention compounds, leaving the opposite enantiomer in solution in a process often referred to as "classical resolution." As one enantiomer of a given invention compound is usually substantially greater in physiological effect than its antipode, this active isomer can thus be found purified in either the crystals or the liquid phase. The salts are produced by reacting the acid form of the invention compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of the present invention have been found to inhibit the matrix metalloproteases MMP-3, MMP-9 and MMP-2, and to a lesser extent MMP-1, and are therefore useful for treating or preventing the conditions referred to in the background section. As other MMPs not listed above share a high degree of homology with those listed above, especially in the catalytic site, it is deemed that compounds of the invention should also inhibit such other MMPs to varying degrees. Varying the substituents on the biaryl portions of the molecules, as well as those of the propanoic or butanoic acid chains of the claimed compounds, has been demonstrated to affect the relative inhibition of the listed MMPs. Thus compounds of this general class can be "tuned" by selecting specific substituents such that inhibition of specific MMP(s) associated with specific pathological conditions can be enhanced while leaving non-involved MMPs less affected.

The method of treating matrix metalloprotease-mediated conditions may be practiced in mammals, including humans, which exhibit such conditions.

The inhibitors of the present invention are contemplated for use in veterinary and human applications. For such purposes, they will be employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art Examples of suitable parenteral administration include intravenous, intraarticular, subcutaneous and intramuscular routes. Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules. Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 $\mu$m) such as those comprising cellulose, polyacrylate or polycarbophil, in conjunction with suitable absorption enhancers such as phospholipids or acylcamitines. Available systems include those developed by DanBiosys and Scios Nova.

A noteworthy attribute of the compounds of the present invention in contrast to those of various peptidic compounds referenced in the background section of this application is the demonstrated oral activity of the present compounds. Certain compounds have shown oral bioavailability in various animal models of up to 90–98%. Oral delivery may be achieved by incorporation of the drug into tablets, coated tablets, dragees, hard and soft gelatine capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azo-crosslinked polymers that are degraded by colon specific bacterial azoreductases, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target enzyme which must be inhibited in order to treat the condition.

The matrix metalloprotease inhibitors of the invention are useful not only for treatment of the physiological conditions discussed above, but are also useful in such activities as purification of metalloproteases and testing for matrix metalloprotease activity. Such activity testing can be both in vitro using natural or synthetic enzyme preparations or in vivo using, for example, animal models in which abnormal destructive enzyme levels are found spontaneously (use of genetically mutated or transgenic animals) or are induced by administration of exogenous agents or by surgery which disrupts joint stability.

EXPERIMENTAL

General Procedures

All reactions were performed in flame-dried or oven-died glassware under a positive pressure of argon and were stirred magnetically unless otherwise indicated. Sensitive liquids and solutions were transferred via syringe or cannula and were introduced into reaction vessels through rubber septa. Reaction product solutions were concentrated using a Buchi evaporator unless otherwise indicated.

Materials

Commercial grade reagents and solvents were used without further purification except that diethyl ether and tetrahydrofuran were usually distilled under argon from benzophenone ketyl, and methylene chloride was distilled under argon from calcium hydride. Many of the specialty organic or organometallic starting materials and reagents were obtained from Aldrich, 1001 West Saint Paul Avenue, Milwaukee, Wis. 53233. Solvents are often obtained from EM Science as distributed by VWR Scientific.

Chromatography

Analytical thin-layer chromatography (MC) was performed on Whatran® pre-coated glass-backed silica gel 60 A F-254 250 µm plates. Visualization of spots was effected by one of the following techniques: (a) ultraviolet illumination, (b) exposure to iodine vapor, (c) immersion of the plate in a 10% solution of phosphomolybdic acid in ethanol followed by heating, and (d) immersion of the plate in a 3% solution of p-anisaldehyde in ethanol containing 0.5% concentrated sulfuric acid followed by heating, and e) immersion of the plate in a 5% solution of potassium permanganate in water containing 5% sodium carbonate followed by heating.

Column chromatography was performed using 230–400 mesh EM Science® silica gel.

Analytical high performance liquid chromatography (HPLC) was performed at 1 mL min$^{-1}$ on a 4.6×250 mm Microsorb® column monitored at 288 nm, and semi-preparative HPLC was performed at 24 mL min$^{-1}$ on a 21.4×250 mm Microsorb® column monitored at 288 nm.

Instrumentation

Melting points (mp) were determined with a Thomas-Hoover melting point apparatus and are uncorrected.

Proton ($^1$H) nuclear magnetic resonance (NMR) spectra were measured with a General Electric GN-OMEGA 300 (300 MHz) spectrometer, and carbon thirteen ($^{13}$C) NMR spectra were X measured with a General Electric GN-OMEGA 300 (75 MHz) spectrometer. Most of the compounds synthesized in the experiments below were analyzed by NMR, and the spectra were consistent with the proposed structures in each case.

Mass spectral (MS) data were obtained on a Kratos Concept 1-H spectrometer by liquid-cesium secondary ion (LCIMS), an updated version of fast atom bombardment (FAB). Most of the compounds systhesized in the experiments below were analyzed by mass spectroscopy, and the spectra were consistent with the proposed structures in each case.

General Comments

For multi-step procedures, sequential steps are noted by numbers. Variations within steps are noted by letters. Dashed lines in tabular data indicates point of attachment

EXAMPLE 1

Preparation of Compound I

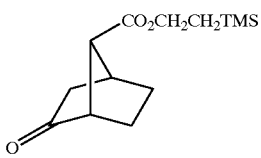

Step 1

A solution of exo-oxobicyclo [2.2.1] heptane-7-carboxylic acid (prepared using the protocols described in Tetrahedron, 37 suppl., 411, 1981) (3.04 g, 19.7 mmol) in CH$_2$Cl$_2$ (45 mL) was cooled to 0° C. and treated with 2-(trimethylsilyl) ethanol (2.7 mL, 18.6 mmol), EDC (3.94 g, 20.55 mmol) and DMAP (0.11 g, 0.9 mmol). After warming to room temperature and stirring for 2 hrs., the reaction mixture was quenched with water and diluted with CH$_2$Cl$_2$. After separating the layers, the organic phase was washed with satd. aq. NaCl, dried over MgSO$_4$ and concentrated. Purification by MPLC (0–25% EtOAc-hexanes) provided the target compound (3.9 g, 78%) as a colorless oil. $^1$H NMR (CDCl$_3$) δ4.18 (m, 2H), 2.88 (m, 2H), 2.76 (m, 1H), 2.05 (m, 4H), 1.50 (m, 2H), 0.99 (t, J=8.4 Hz, 2H), 0.99 (s, 9H).

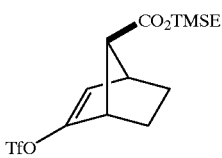

Step 2

A solution of the ketone from step 1 (3.18 g, 12.50 mmol) and 2-[N,N-bis(trifluoromethylsulfonyl)amino]-5-chloropyridine (6.6 g, 16.30 mmol) in THF was cooled to −78° C. and carefully treated with a 0.5M solution of KHMDS in toluene (24 mL, 12 mmol). After the addition was complete and the solution stirred for 2 h, the reaction mixture was quenched with water (30 mL), warmed to room temperature and diluted with EtOAc. The two phases were the separated. The organic layer was washed with satd. aq. NaCl, dried over MgSO$_4$ and concentrated. Purification by MPLC (0–15% EtOAc-hexanes) provided the target compound (4.2 g, 91%) as a colorless oil. $^1$H NMR (CDCl$_3$) δ5.75 (d, J=4.8 Hz, 1H), 4.13 (t, J=9.0 Hz, 2H), 3.18 (m, 2H), 2.62 (m, 1H), 2.62 (m, 2H), 1.41 (t, J=9.3 Hz, 1H), 1.23 (t, J=9.1 Hz, 1H), 0.96 (t, J=8.4 Hz, 2H), 0.04 (s, 9H).

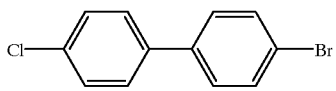

Step 3

A solution of 4chlorobiphenyl (3.0 g, 15.9 mmol) in acetic acid (50 mL) was carefully treated with bromine (1.1 mL, 20.7 mmol) at room temperature. The reaction mixture was heated to reflux for 4 h, cooled to room temperature and treated with excess propene until the mixture became clear. The solution was concentrated to a thick slurry, diluted with CH$_2$Cl$_2$ (50 mL) and washed successively with water and 2N NaOH. The organic extract was dried over MgSO$_4$, filtered and concentrated. Purification by re-crystallization form EtOAc gave the aryl bromide (3.57 g, 84%) as a white crystalline solid. $^1$H NMR (CDCl$_3$) δ7.57 (m, 2H), 7.48 (m, 2H), 7.41 (m, 4H).

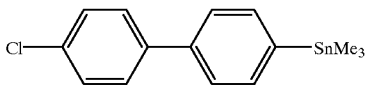

Step 4

A solution of 4-bromo-4'-chlorobiphenyl (8.0 g, 30.0 mmol) in ThF (120 mL) was cooled to −78° C. and carefully treated with n-BuLi (19.7 ml, 1.6 M solution in hexanes, 31.5 mmol). After stirring for 1 h, the mixture was treated with chlorotrimethyltin (33 mL, 1.0 M soln., 33.0 mmol). After an additional 30 min., the solution was warned to room temperature and concnetrated. The off-white solid was diluted with CH$_2$Cl$_2$ (300 mL) and washed successively with water and satd. aq. NaCl. The organic layer was dried over MgSO$_4$, filtered and concentrated. Purification by MPLC (hexanes) gave the desired aryltin compound (9.38 g, 89%) as a white crystalline solid. $^1$H NMR (CDCl$_3$) δ7.62 (m, 6H), 7.54 (m, 2H), 0.39 (s, 9H).

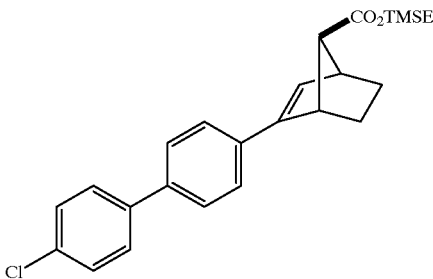

Step 5

A solution of the trrlate from step 2 (4.2 g, 10.89 mmol), CuI (0.215 g, 1.1 mmol), AsPh$_3$ (0.339 g, 1.1 mmol), Cl$_2$Pd(MeCN)$_2$ (0.215 g, 0.56 mmol) and a few crystals of BHT in 1-methyl-2-pyrrolidinone (11.5 mL) was lowered into an oil bath preheated to 85° C. After stirring 4 min., the biphenyltin derivative from step 4 (7.3 g, 20.7 mmol) was added in one portion. The mixture was stirred for 30 min., cooled to room temperature and diluted with EtOAc. After separating the phases, the aq. layer was back extracted with EtOAc and the combined organic layers dried over MgSO$_4$, filtered and concentrated. The resulting residue was adsorbed on silica gel and purified by MPLC (0–15% EtOAc-hexanes) to give the coupled product (4.0 g, 86%) as a white crystalline solid. $^1$H NMR (CDCl$_3$) δ7.52 (m, 6H), 7.42 (n, 2H), 6.40 (d, J=3.3 Hz, 1H), 4.19 (t, J=10.2 Hz, 2H), 3.58 (m, 1H), 3.23 (m, 1H), 2.60 (m, 1H), 1.95 (m, 2H), 1.20 (m, 2H), 1.02 (d, J=7.5 Hz, 2H), 0.08 (s, 9H).

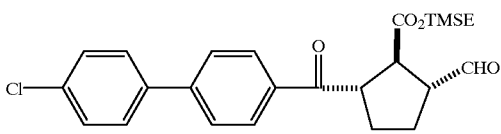

Step 6

A solution of the olefin from step 5 (3.60 g, 8.47 mmol) in 10% MeOH—CH$_2$Cl$_2$ (200 mL) was cooled to −78° C. and treated with ozone as a gas added directly into the reaction mixture (10 min., 1 L/min.). After TLC indicated the absence of starting material the solution was purged with argon (15 min.), treated with methylsulfide (13 mL) and warmed to room temperature. After stirring overnight, the solution was concentrated to a residue which was purified by MPLC (0–15% EtOAc-hexanes) to give a mixture of the desired aldehyde and corresponding dimethyl acetal. The product mixture was dissolved in acetone (45 mL) and treated with CSA (0.192 g, 0.83 mmol) and water (0.13 mL, 16.5 mmol). After stirring overnight, the solution was concentrated and purified by MPLC (0–15% EtOAc-hexanes) to give the desired aldehyde (3.45 g, 89%) as a colorless oil. NMR (CDCl$_3$) δ9.78 (d, J=9.0 Hz, 1H), 8.05 (d, J=6.6 Hz, 2H), 7.65 (d, J=6.6 Hz, 2H), 7.55 (d, J=9.0 Hz, 2H), 7.44 (d, J=9.0 Hz, 2H), 4.15 (m, 3H), 3.87 (t, J=7.2 Hz, 1H), 3.15 (m, 1H), 2.20 (m, 1H), 2.03 (m, 1H), 1.86 (m, 1H), 1.58 (s, 1H), 125 (t, J=6.9 Hz, 1H), 0.93 (m, 2H), 0.00 (s, 9H).

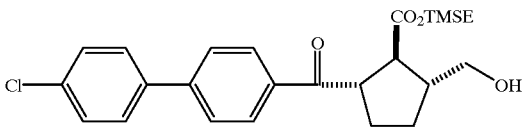

Step 7

A solution of lithium aluminum hydride (1.9 mL, 1.0 M THF) in THF (6 mL) was treated with 3-ethyl-3-pentanol (0.83 g, 5.77 mmol) and heated to a gentle reflux for 1 h. The mixture was then cooled to room temperature.

A solution of the aldehyde intermediate from step 6 (0.85 g, 1.86 mmol) in THF (15 mL) was cooled to −78° C. and treated with the previously prepared solution of LTEPA in THF via cannula in a dropwise manner. After the addition was complete, the solution was stirred at −78° C. for 4 h and subsequently quenched with 2N HCl (4.6 mL). The reaction mixture was diluted with EtOAc and washed with water. The organic layer was dried over MgSO$_4$, filtered and concnetrated. Purification by MPLC (5–40% EtOAc-hexanes) afforded the desired aldehyde (0.640 g, 75%) as a white crystalline solid. $^1$H NMR (CDCl$_3$) δ8.05 (d, J=8.7 Hz, 2H), 7.65 (d, J=8.5 Hz, 2H), 7.55 (d, J=8.4 Hz, 2H), 7.44 (d, J=8.4 Hz, 2H), 4.15 (m, 2H), 3.76 (t, J=6.3 Hz, 2H), 3.28 (t, J=6.3 Hz, 2H), 2.48 (m, 1H), 2.35 (t, J=6.0 Hz, 1H), 2.18 (m, 1H), 1.91 (m, 2H), 1.57 (s, 1H), 1.35 (t, J=6.9 Hz, 1H), 0.91 (m, 2H), −0.01 (s, 9H).

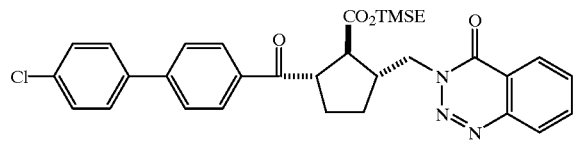

Step 8

A solution of the alcohol from step 7 (0.050 g, 0.109 mmol), triphenylphosphine (0.057 g, 0.217 mmol) and benzo-1,2,3-triazin-4(3H)-one (0.034 g, 0.231 mmol) in THF (2.5 mL) was treated with diethyl azodicarboxylate (0.035 mL, 0.222 mmol). The mixture was stirred at room temperature for 16 hrs., concentrated under reduced pressure and purified by MPLC (0–20% EtOAc-hexanes) to give the target compound (0.034 g, 53%). TLC: R$_f$0.16 (silica, 20% EtOAc-hexanes).

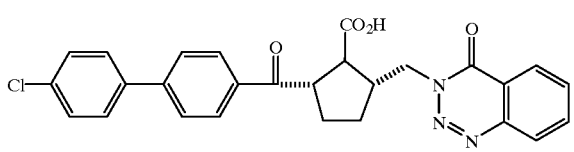

Step 9

A solution of the ester from step 8 (0.031 g, 0.052 mmol) in CH$_2$Cl$_2$ (2 mL) was cooled to 0° C. and treated with TFA (0.25 mL). After stirring for 5 h, the solution was concentrated under reduced pressure and purified via flash column chromatography (0–5% MeOH-CH$_2$Cl$_2$) to give the desired acid (0.023 g, 90%) as a white crystalline solid. MP 198–199° C.

EXAMPLE 2

Preparation of Compound II

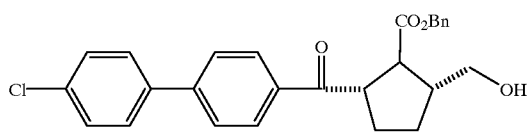

Step 1

The benzyl ester was prepared in a manner analogous to the one described for the corresponding 2-trimethylsilyl ester intermediate (example 1, steps 1–7). In this case, benzyl alcohol was used instead of 2-trimethylsilylethanol in step 1.

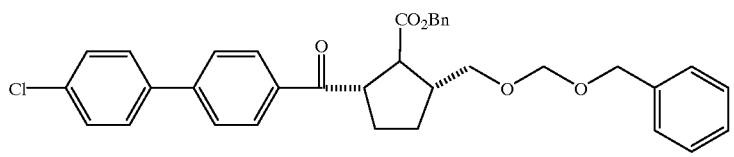

Step 2

A solution of the intermediate from step 1 (0.020 g, 0.045 mmol) and diisopropylethylamine (0.025 mL, 0.144 mmol) in CH$_2$Cl$_2$ (1.5 mL) was treated with benzyl chloromethylether (0.016 mL, 0.099 mmol) and stirred at room temperature for 6 h. Purification of the concentrated reaction mixture, by flash column chromatography (5–20% EtOAc-hexanes) provided the desired ether (0.022 g, 86%). TLC:R$_f$0.25 (silica, 20% EtOAc-hexanes).

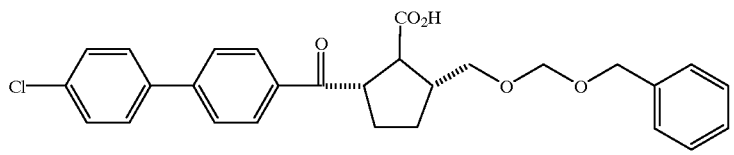

Step 3

A solution of the intermediate benzyl ester from step 2 (0.020 g, 0.035 mmol) in ThF (0.4 mL) and ethanol (0.4mL was treated with NaOH solution (0.14 mL, 0.5 g/10 mL water). After stirring for 45 min At room temperature, the mixture was diluted with EtOAc and quenched with 2N HCl (0.2 ml). The organic layer was washed with satd. aq. NaCl, dried over MgSO$_4$ and concnetrated to give the desired acid (0.012 g, 72%). MP 112–113° C.

EXAMPLE 3

Preparation of Compound III

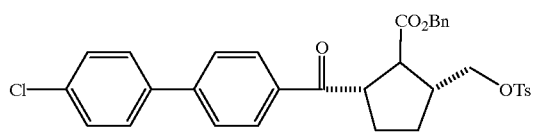

Step 1

A solution of the alcohol from example 2, step 1 (0.100 g, 0.223 mmol) and diisopropylethylamine (0.05 mL, 0.287 mmol) in CH$_2$Cl$_2$ (3.0 mL) was treated with p-toluenesulfonyl chloride (0.048 g, 0.249 mmol) and a crystal of DMAP. The mixture was stirred at room temperature for 16hrs., concentrated under reduced pressure and purified by MPLC (0–20% EtOAc-hexanes) to give the desired tosylate (0.118 g, 88%). TLC:R$_f$0.23 (silica, 0–20% EtOAc-hexanes).

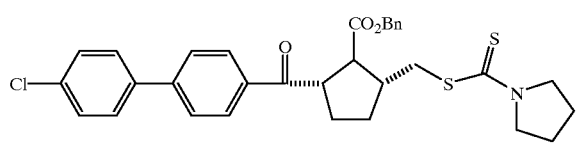

Step 2

A solution of the tosylate from step 1 (0.039 g, 0.066 mmol) and 18-crown-6 (0.044 g, 0.166 mmol) in DMF (0.7 mL) was treated with sodium pyrrolidine dithiocarbamate (0.035 g, 0.165 mmol) and stirred at room temperature for 16 h. The reaction mixture was diluted with EtOAc and water. After separating the phases, the organic layer was washed with satd. aq. NaCl, dried over MgSO$_4$, filtered and concentrated. Purification by MPLC (3–15% EtOAc-hexanes) provided the desired product (0.038 g, 99%). TLC:R$_f$ 0.34 (silica, 0–20% EtOAc-hexanes).

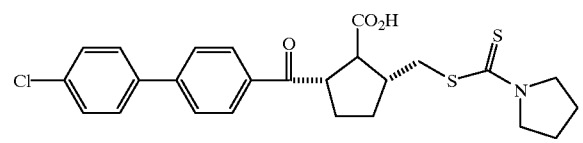

Step 3

The deprotection of the benzyl ester intermediate from step 2 was accomplished using the same protocol as described for example 2 in step 3. MP 177–178° C.

The above methods for preparation of Examples 1–3 were, or could be used to prepare the series of biphenyl containing products found in Table 1.

TABLE 1

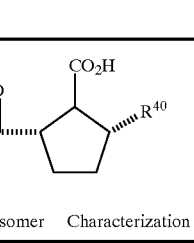

| Example | R$^{40}$ | Isomer | Characterization |
|---------|----------|--------|------------------|
| I       |          | R,S    | MP 198–199° C.   |
| II      | CH$_2$OCH$_2$OCH$_2$Ph | R,S | MP 112–130° C. |
| III     |          | R,S    | MP 177–178° C.   |
| IV      |          | R,S    | R$_f$ 0.33 (silica, 5% MeOH—CH$_2$Cl$_2$) |
| V       |          | R,S    | 219–220° C.      |
| VI      |          | R,S    | 207° C.          |

TABLE 1-continued

| Example | R$^{40}$ | Isomer | Characterization |
|---------|----------|--------|------------------|
| VII     |          | R,S    | 210–211° C.      |
| VIII    |          | R,S    | 290–291° C.      |
| IX      |          |        |                  |
| X       |          |        |                  |
| XI      |          |        |                  |
| XII     |          |        |                  |
| XIII    |          |        |                  |
| XIV     |          |        |                  |

TABLE 1-continued

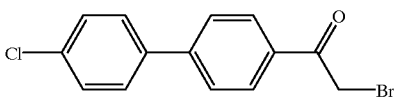

| Example | R40 | Isomer | Characterization |
|---|---|---|---|
| XV | 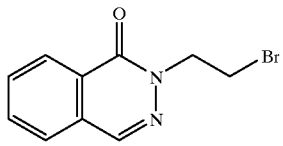 | | |
| XVI | | | |
| XVII | | | |

EXAMPLE 18

Preparation of Compound XVIII

Step 1

A solution of pthlalazinone (1.00 g, 6.84 mmol), triphenylphosphine (1.79 g, 6.84 mmol) in THF (25 mL) was cooled to 0° C. and treated with 2-bromo ethanol (0.480 mL, 6.84 mmol) and diethyl azocrboxylate (1.07 mL, 6.84 mmol). After stirring 1 h at 0° C., the solution was warmed to room temperature and stirred for an additional 12 h. The resulting mixture was concentrated and purified by flash column chromatography (35% ethyl acetate-hexanes) to afford 1.40 g (81%) of bromo ethyl phthalazinone as a white solid. TLC:$R_f$0.65 (40% /ethyl acetate-hexane).

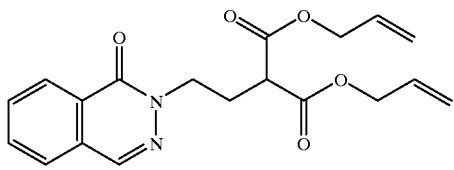

Step 2

A solution of sodium hydride (0.040 g, 1.54 mmol) in THF (5 mL) was cooled to 0° C. and carefully treated with diallyl malonate (0.260 g, 1.41 mmol). After warming to room temperature and stirring for 20 min., bromo ethyl phthalazinone from step 1 (0.325 g, 1.28 mmol) was added in one portion and the mixture was heated to reflux for 18 h. The reaction mixture was diluted with saturated aq. NH$_4$Cl (20 mL) and EtOAc (20 mL). The resulting organic phase was washed with water, dried over MgSO$_4$, filtered, and concentrated to afford 0.240 g (52%) of a yellow oil. TLC:$R_f$0.60 (40% ethyl acetate-hexane).

Step 3

A 2L, three-necked, round bottom flask was equipped with a mechanical stirrer, a thermometer and an argon inlet The flask was charged with a solution of 4-chlorobiphenyl (48.30 g, 0.256 mol) in dichloromethane (500 mL). Bromoacetyl bromide (23 mL, 0.26 mol) was added via syringe and the solution was cooled with an ice bath to an internal temperature of 3° C. The thermometer was temporarily removed and AlCl$_3$ was added portionwise over 5 min. The internal temperature rose to 10° C. and white gas evolved from the opaque olive green reaction mixture. After 24 hrs. of stirring, the reaction was quenched by cautiously pouring into cold 10% HCl (1L). The organic layer became cloudy yellow green. Chloroform was added to help dissolve the solids, but the organic layer never became transparent. The organics were concentrated on a rotary evaporator and dried further under vacuum. The crude product was a pale green solid (~82g) which was recrystallized from hot ethyl acetate to give 1-(2-bromoethanone)-4-(4-chlorophenyl)-benzene as brown needles (58.16 g). Concentration of the mother liquor followed by addition of hexanes delivered a second crop of crystals (11.06 g) which gave an NMR spectrum identical to that of the first crop. The total yield of the product was 87%. TLC:$R_f$0.30 (silica, 70% hexanes-dichloromethane).

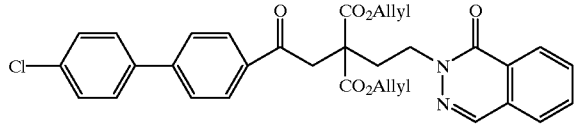

Step 4

A solution of sodium hydride (0.020 g, 0.775 mmol) in THF (2.0 mL) was cooled to 0° C. and carefully treated with the diester from step 2. The ice bath was removed and the resulting mixture was stirred for 20 min. The reaction mixture was re-cooled to 0° C. and treated with 1-(2-bromoethanone)-4-(4-chlorophenyl)benzene (0.200 g, 0.646 mmol) in one portion. The mixture was warmed to room temperature over 30 min and subsequently heated to reflux for 12 hrs. The reaction mixture was added to satd. aq. NH$_4$Cl (10 mL) and diluted with EtOAc (10 mL). The resulting organic phase was washed with water (10 mL), dried over MgSO$_4$, filtered and concentrated to afford 0.327 g (78%) of a yellow oil. TLC:$R_f$0.40 (silica, 40% ethyl acetate-hexane).

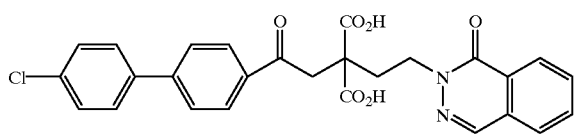

Step 5

A solution of the diester product from step 4 (0.327 g, 0.558 mmol) in 1,4 dioxane (5 mL) was treated with tetris(triphenylphosphine)palladium (0.006 g, 0.005 mmol) in one portion and pyrrolidone (0.102 mL, 1.22 mmol) added dropwise over 15 min. After stirring for 30 min. at room temperature, the reaction mixture was diluted with 1N HCl (20 mL) and EtOAc (20 mL). The resulting organic phase was washed with satd. aq. NaCl, dried over $MgSO_4$, filtered, and concentrated to provide the diacid as a crude brown oil which was immediately carried on to step 6. TLC:$R_f$0.29 (silica, 5% methanol-methylene chloride).

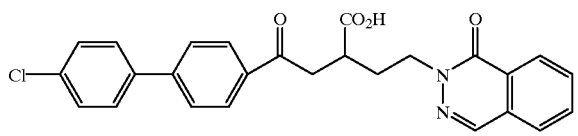

Step 6

A solution of the diacid product from step 5 in 1,4 dioxane (25 mL) was heated to reflux for 24 h. After cooling to room temperature, the resulting mixture was concentrated to a gray solid. Recrystallization from ethyl acetate afforded 0.044g (18%, two steps) of compound XVIII as a white solid. MP 232° C. TLC:$R_f$0.5 (silica, 10% methanol-methylene chloride).

EXAMPLE 19

Preparation of Compound XIX

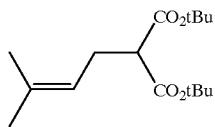

Step 1

A solution of sodium hydride (0.040 g, 1.54 mmol) in THF (100 mL) was cooled to 0° C. and treated with di-tert-butyl malonate (20.7 3 mL, 92.47 mmol) dropwise via dropping funnel, over 20 min. After stirring at room temperature for 30 min., 3,3-dimethylallyl bromide (9.7 mL, 83.22 mmol) was added. After siring an additional 19 h, the reaction mixture was diluted with 10% HCl solution (100 mL) and EtOAc (100 mL). The resulting organic phase was washed with satd. aq. NaCl, dried over $MgSO_4$, filtered, and concentrated to afford 25.74 g (94%)of a crude yellow oil. TLC: $R_f$0.60 (silica, 10% ethyl acetate-hexane).

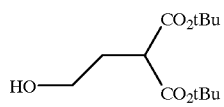

Step 2

A solution of the crude olefin from step 1 (25.74 g, 90.50 mmol) in $CH_2Cl_2$ (350 mL) and methanol (90 mL) was cooled to −78° C. and purged with 02 for 20 min. $O_3$ was bubbled through the solution until a blue color remained (2 h). The solution was purged with $O_2$ for 20 min.; until the solution became colorless. After warming to 0° C., $NaBH_4$ (3.42 g, 90.50 mmol) was added in one portion. After several minutes the ice bath was removed and the mixture was stirred overnight. The mixture was concentrated, reluted in $CH_2Cl_2$, washed with water (100 mL), 10% HCl (100 mL), brine (50 mL), dried over $MgSO_4$, filtered and concentrated into a colorless oil. Purification of 15.0 g of crude material by flash chromatography (30% ethyl acetate-hexanes) afforded 6.86 g (50%) as a colorless oil. TLC:$R_f$0.30 (silica, 35% ethyl acetate-hexane).

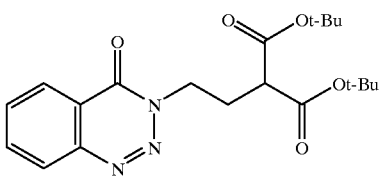

Step 3

The malonate intermediate was prepared in a manner analogous to the one described for the preparation of example 18, step 1. For this example, benzo-1,2,3-triazin-4 (3H)-one was used in place of phthalazinone and the alcohol form step 2 was used in place of 2-bromo ethanol. TLC:$R_f$0.40 (silica, 40% ethyl acetate-hexane).

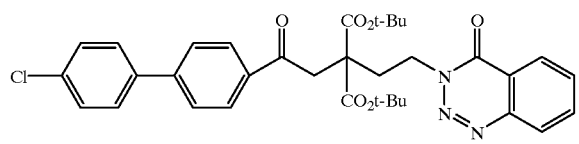

Step 4

The dialkylated malonate intermediate was prepared in a manner analogous to the one described for the preparation of example 18, step 2. In this example, the monoalkylated malonate from step 3 was alkylated with the 1-(2-bromoethone)-4-(4-chlorophenyl)-benzene. TLC:$R_f$0.50 (silica, 40% ethyl acetate-hexane).

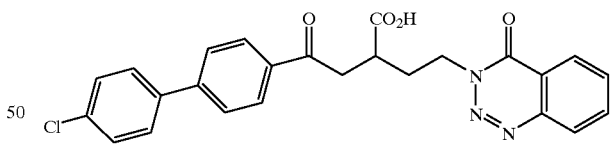

Step 5

A solution of the diester from step 4 (4.61 g, 0.746 mmol) in 1,4 dioxane (10 mL) was treated with 4N HCl and heated to reflux for 10 h. After concnetrating to an oil, the residue was purified by flash chromatography (0–10% methanol-dichloromethane to give a yellow solid. MP 195° C.

EXAMPLE 20 AND EXAMPLE 21

Preparation of compounds XX and XXI

Example 19 was separated by chromatography on a chiral HPLC column ($CH_2Cl_2$EtOAc-hexanes). Example 20 was the first to come off the column. Example 21 eluted second.

Example 20. MS FAB-LSMIS) 462 [M+H]+
Example 21. Anal. Calculated for $C_{25}H_{20}ClN_3O_4$:C, 65.01; H, 4.36; N, 9.10. Found C, 64.70; H, 4.06; N, 8.72.

EXAMPLE 22

Preparation of Compound XXII

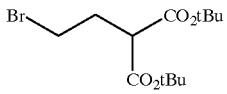

Step 1

A solution of di-tert-butyl (2-hydroxyethyl)malonate (0.500 g, 1.92 mmol), $PPh_3$ (0.555 g, 2.12 mmol) and $CBr_4$ (0.704 g, 2.12 mmol) in $CH_2Cl_2$ (4.0 mL) was stirred at 0° C. for 5 min., then warmed to room temperature. After stirring for an additional 16 h, the reaction mixture was concentrated in vacuo and purified via column chromatography (5–10% ethyl acetate-hexanes) to give 0.615 g (99%) of the desired product. TLC:$R_f$0.7 (silica, 10% EtOAc-hexanes).

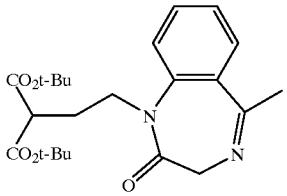

Step 2

A flask containing 1,3-dihydro-5-methyl-2H-1,4-benzodiazepin-2-one (0.324 g, 1.03 mmol) and $CS_2$ $CO_3$ (0.900 g, 2.76 mmol) was dried under vacuum, flushed with Ar and charged with a solution of di-tert-butyl (2-bromoethyl) malonate (0.300 g, 0.929 mmol) in DMF (3.0 mL) at 0° C. The mixture was stirred at 0° C. for 15 min., room temperature for 15 min., and 120° C. for 21 h. The reaction mixture was diluted with EtOAc (250 mL) and washed with water (2×50 mL). The organic layer was separated, dried over $MgSO_4$ and concentrated. Purification by column chromatography (50–100% ethyl acetate-hexanes) afforded 0.017 g of the desired product. TLC:$R_f$0.5 (silica, 100% EtOAc).

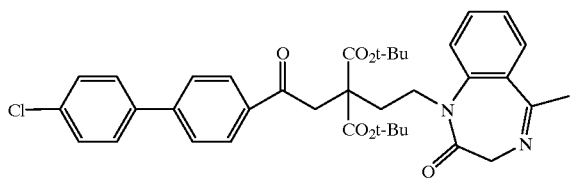

Step 3

A flask containing the mono alkylated malonate from step 2 (0.37 g) and sodium t-butoxide (0.009 g, 0.089 mmol) was vacuum dried, flushed with Ar and diluted with THF (1.0 mL) at 0° C. After stirring at 0° C. for 30 min., the reaction mixture was charged with 4-bromoacetyl4'-chlorobiphenyl (0.027 g, 0.089 mmol) and subsequently stirred at room temperature for an additional 5 h. The reaction mixture was diluted with $CH_2Cl_2$ (75 mL) and washed with water (25 mL). The organic layer was separated, dried over $MgSO_4$ and concentrated. Crude purification by column chromatography (50–100% ethyl acetate-hexanes) afforded the desired product (0.100 g, 0.154 mmol) which was used directly in step 4.

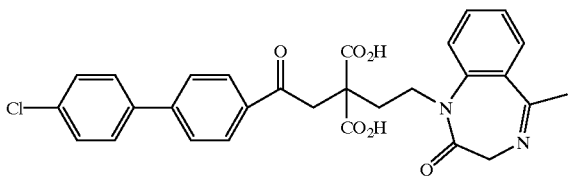

Step 4

A solution of the malonate from step 3 (0.100 g, 0.154 mmol) in formic acid (1.0 mL) was stirred at room temperature for 6 hrs. The resulting solution was concentrated in vacuo and used directly in step 5.

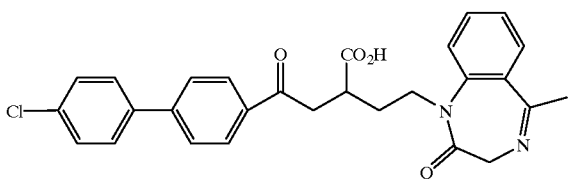

Step 5

A solution of the product from step 4 in 1,4-dioxane (2.0 mL) was heated to 100° C. for 16 h. After cooling to room temperate, the solvent was removed in vacuo. Purification by column chromatography (ethyl acetate-hexanes-AcOH, 60:40:1) afforded 0.020 g of a mixture which contained the desired product. The mixture was purified via HPLC on a C18 column (acetonitrile-water) to furnish 2 mg of the target compound. HRMS 489.15720 (m+1), (calc. 488.15029).

EXAMPLE 23

Biological Assays of Invention Compounds

P218 Quenched Fluorescence Assay for MMP Inhibition

The P218 quenched fluorescence assay (Microfluorometric Profiling Assay) is a modification of that originally described by Knight, et al., FEBS Lett. 296, 263 (1992) for a related substance and a variety of matrix metalloproteinases (MMPs) in cuvettes. The assay was run with each invention compound and the three MMPs, MMP-3, MMP-9 and MMP-2, analyzed in parallel, adapted as follows for a 96-well microtiter plate and a Hamilton AT® workstation.

P218 Fluorogenic Substrate

P218 is a synthetic substrate containing a 4-acetyl-7-methoxycoumarin (MCA) group in the N-terminal position and a 3-[2, 4-dinitrophenyl]-L-2,3-diaminopropionyl (DPA) group internally. This is a modification of a peptide reported by Knight (1992) tat was used as a substrate for matrix metalloproteinases. Once the P218 peptide is cleaved (putative clip site at the Ala-Leu bond), the fluorescence of the MCA group can be detected on a fluorometer with excitation at 328 nm and emission at 393 nm. P218 is currently being produced BACHEM exclusively for Bayer. P218 has the structure:

H-MCA-Pro-Lys-Pro-Leu-Ala-LeuDPA-Ala-Arg-NH2 (MW 1332.2)

Recombinant Human CHO Stromelysin (MMP-3)

Recombinant Human CHO Pro-MMP-3: Human CHO pro-stromelysin-257 (pro-MMP-3) was expressed and purified as described by Housley, et al., J. Biol. Chem. 2, 4481 (1993).

Activation of Pro-MMP-3: Pro MMP-3 at 1.72 μM (100 μg/mL) in 5 mM Tris at pH 7.5, 5 mM CaCl$_2$, 25 mM NaCl, and 0.005% Brij-35 (MMP-3 activation buffer) was activated by incubation with TPCK (N-tosyl-(L)-phenylalanine chloromethyl ketone) trypsin (1:100 w/w to pro-MMP-3) at 25° C. for 30 min. The reaction was stopped by addition of soybean trpsin inhibitor (SBTI;5:1 w/w to trypsin concentration). This activation protocol results in the formation of 45 kDa active MMP-3, which still contains the C-terminal portion of the enzyme.

Preparation of Human Recombinant Pro-Gelatinase A (MMP-2)

Recombinant Human Pro-MMP-2: Human pro-gelatinase A (proMMP-2) was prepared using a vaccinia expression system according to the method of Fridman, et al., J. Biol. Chem. 267, 15398 (1992).

Activation of Pro-MMP-2: Pro-MMP-2 at 252 mg/mL was diluted 1:5 to a final concentration of 50 μg/mL solution in 25 mM Tris at pH 7.5, 5 mM CaCl$_2$, 150 mM NaCl, and 0.005% Brij-35 (MMP-2 activation buffer). p-Aminophenylmercuric acetate (APMA) was prepared in 10 mM (3.5 mg/mL) in 0.05 NaOH. The APMA solution was added at ½₀ the reaction volume for a final AMPA concentration of 0.5 mM, and the enzyme was incubated at 37° C. for 30 min. Activated MMP-2 (15 mL) was dialyzed twice vs. 2 L of MMP-2 activation buffer (dialysis membranes were pre-treated with a solution consisting of 0.1% BSA in MMP-2 activation buffer for 1 min. followed by extensive H$_2$O washing). The enzyme was concentrated on Centricon concentrators (concentrators were also pre-treated a solution consisting of 0.1% BSA in MMP-2 activation buffer for 1 min.. followed by washing with H$_2$O, then MMP-2 activation buffer) with re-dilution followed by re-concentration repeated twice. The enzyme was diluted to 7.5 mL (0.5 times the original volume) with MMP-2 activation buffer.

Preparation of Human Recombinant Pro-Gelatinase B (MMP-9)

Recombinant Human Pro-MMP-9: Human pro-gelatinase B (pro-MMP-9) derived from U937 cDNA as described by Wilhelm, et al. J. Biol. Chem. 264, 17213 (1989) was expressed as the fill-length form using a baculovirus protein expression system. The pro-enzyme was purified using methods previously described by Hibbs, et al. J. Biol. Chem.260, 2493 (1984).

Activation of Pro-MMP-9: Pro-MMP-2 20 μg/mL in 50 mM Tris at pH 7.4, 10 mM CaCl$_2$, 150 mM NaCl, and 0.005% Brij-35 (MMP-9 activation buffer) was activated by incubation with 0.5 mM p-aminophenylmercuric acetate (APMA) for 3.5 h at 37° C. The enzyme was dialyzed against the same buffer to revmove the APMA.

Instrumentation

Hamilton Microlab AT Plus: The MMP-Profiling Assay is performed robotically on a Hamilton MicroLab AT Plus®. The Hamilton is programmed to: (1) serially dilute up to 11 potential inhibitors automatically from a 2.5 mM stock in 100% DMSO; (2) distribute substrate followed by inhibitor into a 96 well Cytofluor plate; and (3) add a single enyme to the plate with mixing to start the Bron. Subsequent plats for each additional enzyme are prepared automatically by beginning the program at the substrate addition point, remixing the diluted inhibitors and beginning the reaction by addition of enzyme. In this way, all MMP assays were done using the same inhibitor dilutions.

Millipore Cytofluor II. Following incubation, the plate was read on a Cytofluor II fluorometric plate reader with excitation at 340 nM and emission at 395 nM with the gain set at 80.

Buffers

Microfluorometric Reaction Buffer (MRB): Dilution of test compounds, enzymes, and P218 substrate for the microfluorometric assay were made in microfluorometric reaction buffer consisting of 50 mM 2-(N-morpholino) ethanesulfonic acid (MES) at pH 6.5 with 10 mM CaCl$_2$, 150 mM NaCl, 0.005% Brij-35 and 1% DMSO.

Methods

MMP Microfluorometric Profiling Assay. The assay is done with a final substrate concentration of 6 μM P218 and approximately 0.5 to 0.8 nM MMP with variable drug concentrations. The Hamilton is programmed to serially dilute up to 11 compounds from a 2.5 mM stock (100% DMSO) to 10x the final compounds concentrations in the assay. Initially, the instrument delivers various amounts of microfluoromentric reaction buffer (MRB) to a 96 tube rack of 1 ml Marsh dilution tubes. The instrument then picks up 20 μl of inhibitor (2.5 mM) from the sample rack and mixes it with a buffer in row A of the Marsh rack, resulting in a 50 μM drug concentration. The inhibitors are then serially diluted to 10, 5, 1, 0.2, 0.05 and 0.01 μM. Position 1 on the sample rack contains only DMSO for the "enzyme-only" wells in the assay, which results in no inhibitor in column 1, rows A through H. The instrument then distributes 107 μl of P218 substrate (8.2 μM in MRB) to a single 96 well cytofluor microtiter plate. The instrument re-mixes and loads 14.5 μl of diluted compound from rows A to G in the Marsh rack to corresponding rows in the microtiter plate. (Row H represents the "background" row and 39.5 μl of MRB is delivered in placed of drug or enzyme). The reaction is started by adding 25 μl of the appropriate enzyme (at 5.86 times the final enzyme concentration) from a BSA treated reagent reservoir to each well, excluding Row H, the "background" row. (The enzyme reservoir is pretreated with 1% BSA in 50 mM Tris,. pH 7.5 containing 150 mM NaCl for 1 hour at room temp., followed by extensive H$_2$O washing and drying at room temp.).

After addition and mixing of the enzyme, the plate is covered and incubated for 25 min. at 37° C. Additional enzymes are tested in the same manner by beginning the Hamilton program with the distribution of P218 substrate to the microtiter plate, followed by re-mixing and distribution of the drug from the same Marsh rack to the microtiter plate. The second (or third, etc.) MMP to be tested is then distributed from a reagent rack to the microtiter plate with mixing, prior to covering and incubation. This is repeated for all additional MMP's to be tested.

IC50 Determination in Microfluorometric Assay: Data generated on the Cytofluor II is copied from an exported ".CSV" file to a master Excel spreadsheet Data from several different MMPs (one 96 well plate per MMP) were calculated simultaneously. The percent inhibition is determination for each drug concentration by comparing the amount of hydrolysis (fluorescence units generated over 25 minutes of hydrolysis) of wells containing compound with the "enzyme only" wells in column 1. Following subtraction of the background the percent inhibition was calculated as:

$$((\text{Control values} - \text{Treated values})/\text{Control values}) \times 100$$

Percent inhibitions were determined for inhibitor concentrations of 5, 1, 0.5, 0.1, 0.02, 0.005 and, 0.001 μM of drug. Linear regression analysis of percent inhibition versus log inhibitor concentration was used to obtain IC$_{50}$ values.

TABLE 2

| Example | MMP-3 Fluorogenic IC$_{50}$ nm | MMP-9 Fluorogenic IC$_{50}$ nm | MMP-2 Fluorogenic IC$_{50}$ nm |
|---|---|---|---|
| 1 | 1.7 | 0.34 | 0.39 |
| 2 | 17 | 24 | 9.5 |
| 3 | 31 | 67 | 21 |
| 4 | 9.2 | 2.1 | 4.2 |
| 5 | 4.2 | 2.3 | 1.4 |
| 6 | 4.1 | 4.3 | 0.5 |
| 7 | 14 | 110 | 10 |
| 8 | 2.0 | 6.2 | 1.0 |
| 18 | 59 | 32 | 13 |
| 19 | 47 | 4.7 | 2.4 |
| 20 | 320 | 84 | 57 |
| 21 | 6.5 | 2.1 | 1.5 |
| 22 | 140 | 120 | 24 |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A matrix metalloprotease inhibitor having the formula:

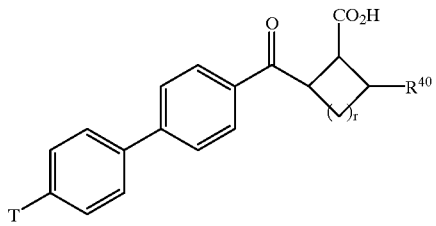

wherein r is 0–2, T is selected from the group consisting of:

 and

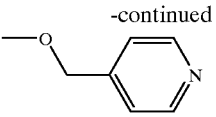

and $R^{40}$ represents

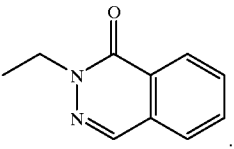

2. A composition having matrix metalloprotease inhibitory activity, comprising a compound of claim 1 and a pharmaceutically acceptable carrier.

3. A method of inhibiting matrix metalloprotease activity in a mammal comprising administration of an effective amount of matrix metalloprotease inhibitor compound of claim 1 to said mammal.

4. The method of claim 3 wherein said mammal is a human.

5. A method of treating a mammal comprising administering to the mammal a matrix metalloprotease inhibiting amount of a compound according to claim 1 sufficient to:

(a) alleviate the effects of osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempero mandibular joint disease, demyelating diseases of the nervous system;

(b) retard tumor metastasis or degenerative cartilage loss following traumatic joint injury;

(c) reduce coronary thrombosis from athrosclerotic plaque rupture; or (d) effect birth control.

6. The method of claim 5 wherein the effect is alleviation of osteoarthritis.

7. The method of claim 5 wherein the effect is retardation of tumor metastasis.

* * * * *